United States Patent
Sad et al.

(10) Patent No.: US 9,539,313 B2
(45) Date of Patent: Jan. 10, 2017

(54) RECOMBINANT BACTERIUM AND USES THEREOF

(71) Applicant: National Research Council of Canada, Ottawa (CA)

(72) Inventors: Subash Sad, Ottawa (CA); Lakshmi Krishnan, Ottawa (CA); Fanny Tzelepis, Ottawa (CA); Valeria Alcon, Ottawa (CA); Kevin G. Young, Ottawa (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 14/516,090

(22) Filed: Oct. 16, 2014

(65) Prior Publication Data

US 2015/0140028 A1   May 21, 2015

Related U.S. Application Data

(63) Continuation of application No. 13/811,690, filed as application No. PCT/CA2011/000848 on Jul. 28, 2011, now abandoned.

(60) Provisional application No. 61/368,346, filed on Jul. 28, 2010.

(51) Int. Cl.
| | |
|---|---|
| A61K 39/00 | (2006.01) |
| A61K 39/12 | (2006.01) |
| C07K 14/195 | (2006.01) |
| C07K 14/47 | (2006.01) |
| C07K 14/705 | (2006.01) |
| C07K 14/71 | (2006.01) |
| C07K 14/77 | (2006.01) |
| C12N 1/20 | (2006.01) |
| C12N 9/36 | (2006.01) |
| C12N 9/64 | (2006.01) |
| C12N 9/02 | (2006.01) |

(52) U.S. Cl.
CPC ....... *A61K 39/0005* (2013.01); *A61K 39/0011* (2013.01); *A61K 39/12* (2013.01); *C07K 14/195* (2013.01); *C07K 14/4713* (2013.01); *C07K 14/4748* (2013.01); *C07K 14/70596* (2013.01); *C07K 14/71* (2013.01); *C07K 14/77* (2013.01); *C12N 1/20* (2013.01); *C12N 9/0059* (2013.01); *C12N 9/2462* (2013.01); *C12N 9/6494* (2013.01); *C12Y 110/03001* (2013.01); *C12Y 304/24011* (2013.01); *A61K 2039/522* (2013.01); *A61K 2039/523* (2013.01); *C07K 2319/036* (2013.01); *C07K 2319/35* (2013.01); *C12N 2760/10034* (2013.01)

(58) Field of Classification Search
None
See application file for complete search history.

(56) References Cited

U.S. PATENT DOCUMENTS

2006/0068469 A1 * 3/2006 Payne et al. ............... 435/69.1

FOREIGN PATENT DOCUMENTS

| | | |
|---|---|---|
| CN | 101204584 | 6/2008 |
| WO | 9853854 | 12/1998 |
| WO | 2006137836 | 12/2006 |
| WO | WO 2007/044406 A2 * | 4/2007 |

OTHER PUBLICATIONS

Bloom et al. J. Exp. Med. 185: 453-459, 1997.*
Igwe et al. Infect. Immun. 70: 7114-7119, 2002.*
Zhu et al. Cancer Science 101: 2621-2628, 2010.*
Panthel et al. Microbes and Infection 8: 2539-2546, 2006.*
English Abstract of CN101204584.
Kotton C. et al., Safety and immunogenicity of attenuated *Salmonella enterica* serovar Typhimurium delivering an HIV-1 Gag antigen via the *Salmonella* Type III secretion system, 2006, Vaccine, vol. 24, pp. 6216-6224.
Shams et al., Induction of specific CD8+ memory T cells and long lasting protection following immunization with *Salmonella typhimurium* expressing a lymphocytic choriomeningitis MHC class I-restricted epitope, 2002, Vaccine, vol. 20, pp. 577-585.
Wang et al., Two oral HBx vaccines delivered by live attenuated *Salmonella*: both eliciting effective anti-tumor immunity, 2008, Cancer Letters, vol. 263, pp. 67-76.
Extended European Search Report issued for corresponding European Patent Application No. 11811675.5.

* cited by examiner

*Primary Examiner* — S. Devi
(74) *Attorney, Agent, or Firm* — Shelly Guest Cermak; Cermak Nakajima & McGowan LLP

(57) ABSTRACT

The present invention relates to a recombinant bacterium expressing an antigen that is translocated to the cytosol of a host organism, and uses thereof. To this end, the present invention provides a recombinant bacterium comprising a nucleic acid encoding an antigen that is translocated to the cytosol of a host cell utilizing Type III secretion system. The recombinant bacterium is generally chosen from intracellular pathogens that reside in the phagosome and fail to induce rapid T cell activation. The translocated antigen may be a viral antigen, a bacterial antigen, or a tumor antigen. Methods of imparting immunity using the recombinant bacterium are also provided.

9 Claims, 19 Drawing Sheets

RECOMBINANT BACTERIUM AND USES THEREOF

CROSS REFERENCE

This application is a continuation of U.S. application Ser. No. 13/811,690 filed Jan. 23, 2013, now abandoned, which is a national stage entry from International Patent Application No. PCT/CA2011/00848 filed Jul. 28, 2011, which in turn claims priority to U.S. Provisional Patent Application No. 61/368,346 filed Jul. 28, 2010, each of which is incorporated herein by reference.

FIELD OF THE INVENTION

The present invention relates to recombinant bacterium and uses thereof. More specifically, the invention relates to recombinant bacterium expressing an antigen that is translocated to the cytosol of a host organism, and uses thereof.

BACKGROUND OF THE INVENTION

Various vaccine vectors or adjuvants that induce potent T cell responses are known in the art (Kaufmann and Hess, 1997). However, very few vaccine vectors exist that induce rapid and potent memory CD8+ cytolytic T cell responses, and that are safe and cost-effective (Raupach and Kaufmann, 2001). Unlike other T cells, CD8+ T cells uniquely provide immune-surveillance to the entire body because they recognize targets in the context of MHC class I molecules, which are present in every cell (Bevan, 1995). Furthermore, CD8+ T cells can eliminate infected cells or tumour cells rapidly. Thus, the induction of specific, potent CD8+ T cells is highly desirable for diseases that are caused by intracellular pathogens and tumours.

Intracellular pathogens induce CD8+ T cell responses; however, the responses are either highly attenuated or the organism itself is highly toxic. Generally, rapid proliferation of pathogens is countered by rapid presentation of antigen to CD8+ T cells within the first few days of infection and activated CD8+ T cells undergo profound expansion (>1000-fold) within the first week of infection, which results in resolution of infection (Kaech and Ahmed, 2001). Similarly, CD8+ T cells play a key role in mediating immune-surveillance against tumours (Smyth et al., 2000). While antibodies and helper T cells mainly promote clearance of extracelluar pathogens (Kaech et al., 2002), CD8+ T cells play a principal role in controlling intracellular pathogens and tumours. Thus, rapid induction of memory CD8+ T cells is essential for developing vaccines against tumours or intracellular pathogens.

While the CD8+ T cells play a key role against various diseases, their induction is highly tedious. Antigenic proteins injected into hosts in the absence or presence of adjuvants does not lead to the induction of CD8+ T cells (Moore et al., 1988). This is mainly because extracelluar proteins do not gain access to the cytoplasm (cytosol) of antigen-presenting cells (APC) (Rock, 1996). Rather, these extracellular proteins or vaccines are trafficked through specialized intracellular vesicles called phagosomes, which leads to the activation of helper T cells to aid antibody production. For induction of CD8+ T cell responses, the pathogen or the vaccine has to reside within the cytosol of an antigen-presenting cell (Bahjat et al., 2006).

Alternative routes of cross-presentation of non-cytosolic antigens to T cells have been suggested (Schaible et al., 2003; Houde et al., 2003; Yrlid and Wick, 2000), however the efficiency of these pathways in controlling pathogens isn't clear (Freigang et al., 2003). Dendritic cells may pick up antigen from dying APCs and present it to CD8+ T cells (Albert et al., 1998). *Salmonella enterica* serovar *Typhimurium* (ST) induces rapid death of macrophages and dendritic cells (Hersh et al., 1999; van der Velden et al., 2000) and it has been shown that cross-presentation of ST antigens occurs through dendritic cells (Yrlid and Wick, 2000). Phagosomes have themselves been considered to be competent at promoting cross-presentation (Houde et al., 2003). However, these mechanisms are of little protective value since rapid pathogen elimination is not observed. Cells that are cross-presenting ST antigens don't appear to serve as good targets for CD8+ T cells to mediate their function. Thus, target cell accessibility seems to be the critical difference between direct and cross-presentation.

Subunit vaccines that consist of purified proteins admixed with adjuvants typically do not induce CD8+ T cell response due to residence of these entities within phagosomes of cells (Bahjat et al., 2006). However, some adjuvants induce CD8+ T cell responses most likely by the cross-presentation pathway (Krishnan et al., 2000). Subunit vaccines are difficult to mass-produce and are faced with numerous technical difficulties including batch to batch variability, quantitation of the antigen-adjuvant ratio, and extensively laborious procedures. To avoid this problem, live vaccines are preferred. However, live vaccines can be either over- or under-attenuated and it is difficult to find the right balance (Raupach and Kaufmann, 2001).

Typically, viral infections (such as Lyphochoriomeningitis virus, LCMV) lead to potent activation of CD8+ T cell responses due to their replication within the cytosol of infected cells (Kaech et al., 2002; Murali-Krishna et al., 1998). However, it is difficult to justify the use of viral vectors as a live vaccine due to the lack of availability of reagents to control the virus, particularly in immunocompromised hosts. Live bacteria can be considered as an alternative option for vaccine development since antibiotics can be used in case they are not controlled by the host. However, extracellular bacteria do not gain access to the cytosol of infected cells, hence fail to induce CD8+ T cell response (Bevan, 1995). On the other hand, intracellular bacteria induce CD8+ T cell response, albeit poor, despite residing within the phagosomes of infected cells, perhaps by cross-presentation (Kaufmann, 1993)—the caveat being that intracellular bacteria (e.g., *Salmonella*, Mycobacteria, *Leishmania*) that reside within the phagosomes of infected cells induce a chronic infection, implying that CD8+ T cells fail to eradicate them from the host (Kaufmann, 1993; Hess and Kaufmann, 1993).

There remains a need in the art for a safe, cost-effective method to induce rapid and potent memory CD8+ cytolytic T cell responses.

SUMMARY OF THE INVENTION

The present invention relates to recombinant bacterium and uses thereof. More specifically, the invention relates to recombinant bacterium expressing an antigen that is translocated to the cytosol of a host organism, and uses thereof.

The present invention provides a recombinant bacterium, comprising a nucleic acid encoding an antigen that is translocated to the cytosol of a host cell. The bacterium may be *Salmonella*, Mycobacteria, *Brucella*, or *Leishmania*. In one example, the recombinant bacterium may be *Salmonella*.

The antigen expressed by the recombinant bacteria as just described may be a viral antigen, a bacterial antigen, or a tumour antigen. The antigen may be the nucleoprotein of LCMV, tyrosinase related protein 2 (TRP-2), MART-1, melanoma associated antigen 1 (MAGE1), gp100, or Her-2/neu or other viral or bacterial antigens.

The nucleic acid encoding the antigen may encode a fusion protein comprising the antigen and a translocation domain from a type III secretion system. For example, the translocation domain may be YopE, SopE, SptP, or a fragment thereof; in one specific example, the chaperone may be SycE or a fragment thereof (such as, but not limited to MKISSFISTSLPLPTSVS, SEQ ID NO:2). The fusion protein may optionally further comprise a chaperone. The chaperone may be derived from a type III secretion system. For example, the chaperone may be SycE or HSP70.

The nucleic acid may be comprised in a vector. The vector may be a pHR vector; in a specific example, the vector may be a modified pHR-241 vector. In the modified pHR-241 vector, the vector may be modified to remove the sequence of p60/M45, may be optionally further modified to remove the sequence of SycE.

Specific, non-limiting examples of fusion proteins encompassed by the present invention are those of SEQ ID NO:7 to SEQ ID NO:12.

The present invention also provides a method of imparting immunity against naturally-occurring bacterium in a subject, the method comprising administering the recombinant bacterium described above to said subject.

The present invention further provides a method of imparting immunity against tumours in a subject, the method comprising administering the recombinant bacterium described above to said subject. The recombinant bacterium may be administered by intravenous, oral, or subcutaneous routes of immunization.

The present invention also encompasses a use of the recombinant bacterium described herein as a vaccine.

Previously, it was known that pathogen-specific CD8+ T cells remain ineffective as long as the pathogen remained in the phagosome. For example, when conventional memory CD8+ T cells against a given antigen were adoptively transferred to naïve hosts, they failed to respond rapidly in response to the same antigen expressed by ST infection (Luu et al., 2006). Presently, a recombinant ST that injects an antigen directly into the host cytosol has been developed. This results in profound CD8+ T cell activation and consequent elimination of ST. It is also shown that when CD8+ T cells are engaged in this manner, they undergo profound expansion which results in massive pathogen and tumour control as well as abridgment of pathogen chronicity. For example, as is evident in present FIG. 3E, the numbers of OVA-specific CD8+ T cells were similar at day 60 in ST-OVA-T versus ST-OVA-NT groups, but the burden was controlled only in the ST-OVA-T infected group, reiterating the notion that antigenic accessibility is the key to CD8+ T cell functionality. This strategy works even with attenuated strains of Salmonella.

Notwithstanding the numerous genes that pathogens such as ST employ for virulence and chronicity (Jones and Falkow, 1996; Kaufmann et al., 2001), the present data provide novel insights into the incapacity of the immune system to efficiently control the bacterium, as well as reveal the power of the acquired immune system, wherein engagement of potent antigen-presentation early on can be sufficient to control an otherwise uncontrollable bacterium. The present results provide compelling evidence that modulation of the cell biology of antigen trafficking is a key avenue that is employed by various pathogens for immune evasion. Thus, a novel vaccine vector (Salmonella) is presently provided, wherein a key modification makes the bacterium generate rapid, potent CD8+ T cell response, resulting in self-destruction of the vaccine in vivo, making it highly efficacious, safe and cost-effective at the same time.

The use of OVA as an antigen is described herein as a proof of principle. Using a similar approach, other putative antigens from other pathogens (bacteria, virus) or tumours can be cloned into ST and these antigens can be translocated into the host cell cytosol for rapid and potent antigen-presentation using the YopE/SycE system. When a tumour-antigen is cloned into ST using the YopE/SycE system, potent and rapid anti-tumour CD8+ T cell response is generated which consequently results in rapid destruction of the bacterium.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 2A shows a graph representing the doubling times of the ST-OVA-NT (closed circles) and ST-OVA-T (open circles) bacteria in liquid culture, based on the measurement of OD at 600 nm. Based on these values, the bacteria were found to be similar.

FIG. 14A shows the schematic representation of the full length (upper panel) and the truncated YopE (lower panel). FIG. 14B shows the OVA-specific CD8+ T cell response in the spleens of mice infected with full YopE or truncated YopE. FIG. 14C shows that both the full length and truncated YopE induce the rapid generation of OVA-specific CD8+ T cells expressing memory marker (CD127). FIG. 14D shows the inflammation induced (numbers of spleen cells) in mice infected with full length or truncated YopE. FIG. 14E shows the bacterial burden in the spleens of mice infected with full length or truncated YopE. ST-OVA-NT (closed circles); ST-OVA-T (open circles); ST-OVA-tYopE (closed triangles).

DETAILED DESCRIPTION OF THE INVENTION

Figure 1A:
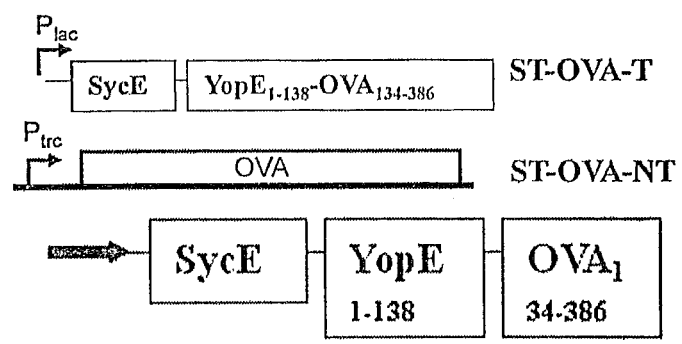
FIG. 1A shows a schematic of the fusion protein constructed, where an antigen (OVA) is fused to YopE, which is then incorporated into the plasmid pHR241 containing the SycE chaperone.

The present invention relates to recombinant bacterium and uses thereof. More specifically, the invention relates to recombinant bacterium expressing an antigen that is translocated to the cytosol of a host organism, and uses thereof.

The present invention provides a recombinant bacterium, comprising a nucleic acid encoding an antigen that is translocated to the cytosol of the host organism.

The bacterium may be any virulent or attenuated bacterium that resides in the phagosome of macrophages and/or dendritic cells and induces poor T cell activation. Such a bacterium may be, but is not limited to *Salmonella*, Mycobacteria, *Brucella, Leishmania*, and the like, which are all intracellular pathogens that reside in the phagosome and fail to induce rapid T cell activation, hence causing diseases that are not controlled by the immune system.

In one example, the virulent or attenuated bacterium may be *Salmonella*. Any suitable strain of *Salmonella* known in the art may be used; for example, and without wishing to be limiting in any manner, the virulent or attenuated bacterium may be *Salmonella enterica*, serovar *Typhimurium* (ST). ST is a highly virulent pathogen that induces gastroenteritis in humans, and typhoid-like disease in mice (Jones and Falkow, 1996). In susceptible C57BL/6J mice, which lack natural resistance-associated macrophage proteins (NRAMP), ST (strain SL1344) induces a systemic lethal infection even at doses as low as ($10^2$) (iv), and all mice die within 7 days of infection (Albaghdadi et al., 2009). In contrast, ST induces a chronic but non-lethal infection in resistant 129SvJ mice (which express NRAMP). F1 hybrids between susceptible and resistant mice (B6.129F1) also harbour a chronic, non fatal, infection (Luu et al., 2006). Genes that are involved in *Salmonella* invasion of epithelial cells are clustered at the *Salmonella* pathogenicity island-1 loci (SPI-1) (Bliska et al., 1993; Zhou and Galan, 2001; Galan and Curtiss, III, 1989; Hardt et al., 1998). They encode several factors, including a type III secretion system (TTSS) apparatus that exports specific proteins (effectors) into the host cell. Two major virulence loci allow *Salmonella* to survive inside cells (Jones and Falkow, 1996). The two-component regulatory system phoP/phoQ, which controls >40 genes (Groisman et al., 1989; Miller et al., 1989), is involved in intracellular survival (Garvis et al., 2001). Another pathogenicity island (SPI-2) encodes a second TTSS, mediates resistance to intracellular killing, and is key to virulence (Hensel et al., 1995; Shea et al., 1996).

The CD8+ T cell response against ST is delayed, which fails to control the bacterium leading to a chronic infection (Albaghdadi et al., 2009). aroA mutant of ST was developed as a vaccine against *Salmonella* (Hoiseth and Stocker, 1981), which induces minimal inflammation and poor immunogenicity (Albaghdadi et al., 2009; Dudani et al., 2008). The virulent or attenuated bacterium of the present invention may be the aroA mutant of ST, comprising a vaccine vector modified such that the bacterium resides in the phagosome of infected cells, but translocates antigen to the cytosol. This modification allows rapid induction of CD8+ T cells; without wishing to be bound by theory, this may lead to the self-destruction of the vaccine. Phagosomal localization is considered a major impediment to T cell activation, and the antigenic translocation strategy described herein can be used for other intracellular bacterial vaccine vectors, including Mycobacteria, *Brucella* or *Leishmania*.

By the term "recombinant" it is meant that the bacterium has been genetically altered or engineered; such genetic engineering may be the inclusion of a recombinant (or artificial) nucleic acid or vector (comprising a nucleic acid) encoding a foreign protein that is an antigen.

The antigen may be any suitable protein or fragment thereof that is processed and presented efficiently by dendritic cells and/or macrophages resulting in efficient T cell activation. Without wishing to be limiting in any manner, the antigen or fragment thereof may be a nascent protein, a bacterial antigen, viral antigen, or a tumour antigen. For example, the antigen may be, but is not limited to tyrosinase related protein 2 (TRP-2), MART-1, melanoma associated antigen 1 (MAGE1), gp100, Her-2/neu or other proteins or fragments thereof known in the art. Other proteins may include, but are not limited to ovalbumin, hen egg lysozyme, and myelin basic protein, nuclear protein of LCMV. In a specific, non-limiting example, the antigens may be ovalbumin, TRP-2, gp-100, LCMV-NP, or fragments thereof.

Upon infection, the antigen is translocated into the cytosol of the host cell (for example macrophages and/or dendritic cells). The antigen may naturally translocate to the cytosol, or may be a recombinant protein engineered to do so. Thus, the antigen may be comprised in a fusion protein that further comprises a translocation domain from a type III secretion system; optionally, the fusion protein may further comprise a chaperone. As would be known to those of skill in the art, the fusion protein, also referred to herein as "fused proteins", comprising the antigen may be generated via recombinant methods well-known to those of skill in the art. The antigen and translocation domain, and the optional chaperone, may be joined directly or by a linker; appropriate linkers would be well-known to those of skill in the art.

By the term "translocation domain", it is meant a protein domain or fragment thereof that directs translocation of a protein from the phagosome to the cytosol of the host cell. The translocation domain may be any suitable translocation domain from known type III secretion systems of bacteria, which are well-known to those of skill in the art. For example, and without wishing to be limiting in any manner, the translocation domain may be YopE or a fragment thereof. YopE is a 23 kDa protein comprising a N-terminal secretion domain of approximately 11 amino acids and a translocation domain of at least 50 aa. In one specific, non-limiting example, the YopE translocation domain may comprise the sequence:

```
                                              (SEQ ID NO: 1)
MKISSFISTSLPLPTSVSGSSSVGEMSGRSVSQQKSEQYANNLAGRT

ESPQGSSLASRITEKLSSMARSAIEFIKRMFSEGSHKPVVTPAPTPA

QMPSPTSFSDSIKQLAAETLPKYIQQLSSLDAETLQKNHDQFAT,
``` a fragment thereof (such as, but not limited to MKISSFIST-SLPLPTSVS, SEQ ID NO:2), or a sequence substantially identical thereto. Another suitable translocation domain may be the SptP protein of ST (Russmann et al., 1998); again, the SptP translocation domain could be the full length protein or a truncated version thereof. In one specific example, the SptP translocation domain may comprise the sequence:

```
                                              (SEQ ID NO: 3)
MLKYEERKLNNLTLSSFSKVGVSNDARLYIAKENTDKAYVAPEKFSS

KVLTWLGKMPLFKNTEVVQKHTENIRVQDQKILQTFLHALTEKYGET

AVNDALLMSRINMNKPLTQRLAVQITECVKAADEGFINLIKSKDNVG

VRNAALVIKGGDTKVAEKNNDVGAESKQPLLDIALKGLKRTLPQLEQ

MDGNSLRENFQEMASGNGPLRSLMTNLQNLNKIPEAKQLNDYVTTLT

NIQVGVARFSQWGTCGGEVERWVDKASTHELTQAVKKIHVIAKELKN
```

-continued
VTAELEKIEAGAPMPQTMSGPTLGLARFAVSSIPINQQTQVKLSDGM

PVPVNTLTFDGKPVALAGSYPKNTPDALEAHMKMLLEKECSCLVVLT

SEDQMQAKQLPPYFRGSYTFGEVHTNSQKVSSASQGEAIDQYNMQLS

CGEKRYTIPVLHVKNWPDHQPLPSTDQLEYLADRVKNSNQNGAPGRS

SSDKHLPMIHCLGGVGRTGTMAAALVLKDNPHSNLEQVRADFRDSRN

NRMLEDASQFVQLKAMQAQLLMTTAS, a fragment thereof, or a sequence substantially identical thereto. Yet another example of a suitable translocation domain is SopE, a type III secretion protein in *Salmonella* ST (Zhu et al., 2010). In a specific example, the SopE translocation domain may comprise the sequence:

(SEQ ID NO: 4)
MTKITLSPQNFRIQKQETTLLKEKSTEKNSLAKSILAVKNHFIELRS

KLSERFISHKNTESSATHFHRGSASEGRAVLTNKVVKDFMLQTLNDI

DIRGSASKDPAYASQTREAILSAVYSKNKDQCCNLLISKGINIAPFL

QEIGEAAKNAGLPGTTKNDVFTPSGAGANPFITPLISSANSKYPRMF

INQHQQASFKIYAEKIIMTEVAPLFNECAMPTPQQFQLILENIANKY

IQNTP, a fragment thereof, or a sequence substantially identical thereto.

The fusion protein may optionally comprise a chaperone. By the term "chaperone", it is meant a protein that assists in translocation of the immunodominant antigen. The chaperone protein may be any suitable protein known in the art, and must be compatible with translocation domain chosen. The chaperone may also be from a type III secretion system. For example, and without wishing to be limiting, the chaperone may be SycE. SycE is a YopE-specific chaperone that is required for YopE-mediated translocation of fused proteins to the cytosol (Russmann et al., 2001). SycE assists in translocation of the fused protein into the cytosol of infected cells through the type III secretion system of ST. In a specific, non-limiting example, the SycE chaperone may comprise the sequence:

(SEQ ID NO: 5)

MYSFEQAITQLFQQLSLSIPDTIEPVIGVKVGEFACHITEHPVGQIL

MFTLPSLDNNNEKETLLSHNIFSQDILKPILSWDEVGGHPVLWNRQP

LNNLDNNSLYTQLEMLVQGAERLQTSSLISPPRSFS, or a sequence substantially identical thereto. In another example, the SopE translocation domain has been used in combination with the chaperone protein heat shock protein 70 (Hsp70) to deliver an antigen to the cytosol (Zhu et al., 2010). In a specific, non-limiting example, the chaperone may comprise the sequence:

(SEQ ID NO: 6)

MGKIIGIDLGTTNSCVAIMDGTQARVLENAEGDRTTPSIIAYTQDGE

TLVGQPAKRQAVTNPQNTLFAIKRLIGRRFQDEEVQRDVSIMPYKII

GADNGDAWLDVKGQKMAPPQISAEVLKKMKKTAEDYLGEPVTEAVIT

-continued

VPAYFNDAQRQATKDAGRIAGLEVKRIINEPTAAALAYGLDKEVGNR

TIAVYDLGGGTFDISIIEIDEVDGEKTFEVLATNGDTHLGGEDFDTR

LINYLVDEFKKDQGIDLRNDPLAMQRLKEAAEKAKIELSSAQQTDVN

LPYITADATGPKHMNIKVTRAKLESLVEDLVNRSIEPLKVALQDAGL

SVSDINDVILVGGQTRMPMVQKKVAEFFGKEPRKDVNPDEAVAIGAA

VQGGVLTGDVKDVLLLDVTPLSLGIETMGGVMTPLITKNTTIPTKHS

QVFSTAEDNQSAVTIHVLQGERKRASDNKSLGQFNLDGINPAPRGMP

QIEVTFDIDADGILHVSAKDKNSGKEQKITIKASSGLNEEEIQKMVR

DAEANAESDRKFEELVQTRNQGDHLLHSTRKQVEEAGDKLPADDKTA

IESALNALETALKGEDKAAIEAKMQELAQVSQKLMEIAQQQHAQQQA

GSADASANNAKDDDVVDAEFEEVKDKK, or a sequence substantially identical thereto. The inclusion of the chaperone is optional, as the translocation domain, or a fragment thereof, alone may be sufficient to cause translocation of the antigen to the cytosol; for example, and without wishing to be limiting, YopE alone, or an 18-amino acid fragment thereof (MKISSFISTSLPLPTSVS, SEQ ID NO:2) are presently shown to produce the desired effect. Similarly, expression of the endogenous *Salmonella* chaperone protein InvB is sufficient to mediate the translocation function of SopE (Lee and Galan, 2003).

In one specific example of the present invention, the recombinant bacterium comprises a nucleic acid encoding an antigen comprising a fusion protein comprising the sequence of SycE, YopE, and ovalbumin:

(SEQ ID NO: 7)

MYSFEQAITQLFQQLSLSIPDTIEPVIGVKVGEFACHITEHPVGQIL

MFTLPSLDNNNEKETLLSHNIFSQDILKPILSWDEVGGHPVLWNRQP

LNNLDNNSLYTQLEMLVQGAERLQTSSLISPPRSFSMKISSFISTSL

PLPTSVSGSSSVGEMSGRSVSQQKSEQYANNLAGRTESPQGSSLASR

ITEKLSSMARSAIEFIKRMFSEGSHKPVVTPAPTPAQMPSPTSFSDS

IKQLAAETLPKYIQQLSSLDAETLQKNHDQFATGSNFQTAADQAREL

INSRVESQTNGIIRNVLQPSSVDSQTAMVLVNAIVFKGLWEKAFKDE

DTQAMPFRVTEQESKPVQMMYQIGLFRVASMASEKMKILELPFASGT

MSMLVLLPDEVSGLEQLESIINFEKLTEWTSSNVMEERKIKVYLPRM

KMEEKYNLTSVLMAMGITDVFSSSANLSGISSAESLKISQAVHAAHA

EINEAGREVVGSAEAGVDAASVSEEFRADHPFLFCIKHIATNAVLFF

GRCVSP, a fusion protein comprising the sequence of SycE, a fragment of YopE, and ovalbumin:

(SEQ ID NO: 8)

MYSFEQAITQLFQQLSLSIPDTIEPVIGVKVGEFACHITEHPVGQIL

MFTLPSLDNNNEKETLLSHNIFSQDILKPILSWDEVGGHPVLWNRQP

LNNLDNNSLYTQLEMLVQGAERLQTSSLISPPRSFSMKISSFISTSL

PLPTSVSGSNFQTAADQARELINSRVESQTNGIIRNVLQPSSVDSQT

```
AMVLVNAIVFKGLWEKAFKDEDTQAMPFRVTEQESKPVQMMYQIGLF

RVASMASEKMKILELPFASGTMSMLVLLPDEVSGLEQLESIINFEKL

TEWTSSNVMEERKIKVYLPRMKMEEKYNLTSVLMAMGITDVFSSSAN

LSGISSAESLKISQAVHAAHAEINEAGREVVGSAEAGVDAASVSEEF

RADHPFLFCIKHIATNAVLFFGRCVSP,
``` a fusion protein comprising the sequence of a fragment of YopE and ovalbumin:

```
                                    (SEQ ID NO: 9)
MKISSFISTSLPLPTSVSGSNFQTAADQARELINSRVESQTNGIIRN

VLQPSSVDSQTAMVLVNAIVFKGLWEKAFKDEDTQAMPFRVTEQESK

PVQMMYQIGLFRVASMASEKMKILELPFASGTMSMLVLLPDEVSGLE

QLESIINFEKLTEWTSSNVMEERKIKVYLPRMKMEEKYNLTSVLMAM

GITDVFSSSANLSGISSAESLKISQAVHAAHAEINEAGREVVGSAEA

GVDAASVSEEFRADHPFLFCIKHIATNAVLFFGRCVSP,
``` a fusion protein comprising the sequence of SycE, YopE, and TRP-2:

```
                                    (SEQ ID NO: 10)
MYSFEQAITQLFQQLSLSIPDTIEPVIGVKVGEFACHITEHPVGQILMFT

LPSLDNNNEKETLLSHNIFSQDILKPILSWDEVGGHPVLWNRQPLNNLDN

NSLYTQLEMLVQGAERLQTSSLISPPRSFSMKISSFISTSLPLPTSVSGS

SSVGEMSGRSVSQQKSEQYANNLAGRTESPQGSSLASRITEKLSSMARSA

IEFIKRMFSEGSHKPVVTPAPTPAQMPSPTSFSDSIKQLAAETLPKYIQQ

LSSLDAETLQKNHDQFATMKISSFISTSLPLPTSVSGSSSVGEMSGRSVS

QQKSEQYANNLAGRTESPQGSSLASRITEKLSSMARSAIEFIKRMFSEGS

HKPVVTPAPTPAQMPSPTSFSDSIKQLAAETLPKYIQQLSSLDAETLQKN

HDQFATGSGILLRARAQFPRVCMTLDGVLNKECCPPLGPEATNICGFLEG

RGQCAEVQTDTRPWSGPYILRNQDDREQWPRKFFNRTCKCTGNFAGYNCG

GCKFGWTGPDCNRKKPAILRRNIHSLTAQEREQFLGALDLAKKSIHPDYV

ITTQHWLGLLGPNGTQPQIANFSVYDFFVWLHYYSVRDTLLGPGRPYKAI

DFSHQGPAFVTWH,
``` a fusion protein comprising the sequence of SycE, YopE, and gp100:

```
                                    (SEQ ID NO: 11)
MYSFEQAITQLFQQLSLSIPDTIEPVIGVKVGEFACHITEHPVGQILMFT

LPSLDNNNEKETLLSNIFSQDILKPILSWDEVGGHPVLWNRQPLNSLDNN

SLYTQLEMLVQGAERLQTSSLISPPRSFSMKISSFISTSLPLPASVSGSS

SVGEMSGRSVSQQKSDQYANNLAGRTESPQGSSLASRIIERLSSMAHSVI

GFIQRMFSEGSHKPVVTPALTPAQMPSPTSFSDSIKQLAAETLPKYMQQL

SSLDAETLQKNHDQFATGSGKNTMDLVLKRCLLHLAVIGALLAVGATKVP

RNQDWLGVSRQLRTKAWNRQLYPEWTEAQRLDCWRGGQVSLKVSNDGPTL

IGANASFSIALNFPGSQKVLPDGQVIWVNNTIINGSQVWGGQPVYPQETD

DACIFPDGGPCPSGSWSQKRSFVYVWKTWGQYWQVLGGPVSGLSIGTGRA

MLGTHTMEVTVYHRRGSRSYVPLAHSSSAFTITDQVPFSVSVSQLRALDG

GNKHFLRNQPLTFALQLHDPSGYLAEADLSYTWDFGDSSGTLISRALWTH

TYLEPGPVTAQWLQAAI PLT,
``` a fusion protein comprising the nuclear protein of SycE, YopE, and LCMV-NP:

```
                                    (SEQ ID NO: 12)
MYSFEQAITQLFQQLSLSIPDTIEPVIGVKVGEFACHITEHPVGQILMFT

LPSLDNNNEKETLLSHNIFSQDILKPILSWDEVGGHPVLWNRQPLNNLDN

NSLYTQLEMLVQGAERLQTSSLISPPRSFSMKISSFISTSLPLPTSVSGS

SSVGEMSGRSVSQQKSEQYANNLAGRTESPQGSSLASRITEKLSSMAHSA

IEFIKRMFSEGSHKPVVTPAPTPAQMPSPTSFSDSIKQLAAETLPKYMQQ

LSSLDAETLQKNHDQFATGSFVSDQVGDRNPYENILYKVCLSGEGWPYIA

CRTSIVGRAWENTTIDLTSEKPAVNSPRPAPGAAGPPQVGLSYSQTMLLK

DLMGGIDPNAPTWIDIEGRFNDPVEIAIFQPQNGQFIHFYREPVDQKQFK

QDSKYSHGMDLADLFNAQPGLTSSVIGALPQGMVLSCQGSDDIRKLLDSQ

NRKDIKLIDVEMTREASREYEDKVWDKYGWLCKMHTGIVRD,
``` or a sequence substantially identical thereto. The fusion protein further comprises the sequence of the antigen of interest.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 70%, 80%, 90%, or 95% identical; in another example, the substantially identical sequences may be at least 70, 71, 72, 73, 74, 75, 80, 85, 90, 95, 96, 97, 98, 99, or 100% identical at the amino acid level to sequences described herein. Importantly, the substantially identical sequences retain the activity and specificity of the reference sequence.

The present invention also encompasses nucleic acids encoding the antigen as described above, as well as vectors comprising the nucleic acid.

Thus, the recombinant bacterium of the present invention may comprise a nucleic acid encoding the antigen as described above, or may comprise a vector (also referred to herein as "plasmid") comprising such nucleic acid that is fused with the nucleic acid of a translocation domain and optionally the nucleic acid of a chaperone; for example, and without wishing to be limiting in any manner, the vector in which antigen is translocated to the cytosol of infected cells may be a modified pHR plasmid. The modified pHR construct uses the type III secretion protein to generate fusion proteins that are transported out of the phagosome and through the host bacterial type III secretion system for direct cytosolic antigen presentation. The pHR constructs may comprise sequences encoding a translocation domain and optionally a chaperone protein to aid in proper trafficking of the downstream fusion protein. In a specific, non-limiting example, the vector may be a modified pHR-241 plasmid (Russmann et al., 2001); more specifically, the pHR-241 comprising the sequence of SycE-YopE-p60/M45 fusion protein (Russmann et al., 2000) modified to remove the sequence of p60/M45. In another example, the pHR241 vector is modified to comprise YopE or a fragment of YopE (for example, but not limited to MKISSFISTSLPLPTSVS, SEQ ID NO:2) with the sequence for the SycE and p60/M45 proteins removed. Replacement of the antigenic sequence by appropriate restriction enzymes and subsequent ligation of other antigens would result in development of the desired CD8+ T cell response against said antigens upon vaccination. Furthermore, the recombinant bacterium that harbors this plasmid need not be a highly virulent bacterium; for example, attenuated *Salmonella* is presently shown to be effective at inducing the desired response. The response can be accentuated further by vaccination with higher doses of the attenuated strain.

The recombinant bacterium as described above may be utilized to impart immunity against other naturally-occurring and virulent bacteria. This may be accomplished by administering an effective amount of the recombinant bacterium of the present invention to a subject, and allowing a CD8+ T cell response to be mounted. Similarly, the recombinant bacterium may be utilized to impart immunity against tumors in a subject, by administering an effective amount of the recombinant bacterium of the present invention to said subject. In both methods, the recombinant bacterium may be administered through intravenous, oral or subcutaneous routes of immunization. This approach avoids the unwanted side-effects of persisting bacteria and undesirable toxicity/inflammation associated with live vaccines. Thus, higher doses of the vaccine can be used for improved efficacy. Because the recombinant bacterium of the present invention is eliminated after a few weeks, there is little concern regarding toxicity. Furthermore, *Salmonella* when given orally induces a mucosal CD8+ T cell response (Jones and Falkow, 1996). Thus, the modified bacterium can be administered through the oral route for induction of the desired CD8+ T cell response.

The recombinant bacterium as described above may also be utilized as a vaccine; the vaccine may protect against other naturally-occurring and virulent bacteria, other bacterial pathogens, viral pathogens, or tumors. When the antigen is a tumour-antigen, the tumour-antigen will be translocated to the host cell cytosol, resulting in rapid activation of tumor-specific CD8+ T cells, which will translate to better tumour control by tumor-specific CD8+ T cells.

A recombinant ST that injects an antigen directly into the host cytosol has presently been developed. This results in profound CD8+ T cell activation and consequent elimination of ST. It is also shown that when CD8+ T cells are engaged in this manner, they undergo profound expansion which results in massive pathogen and tumour control as well as abridgment of pathogen chronicity. The present data provide novel insights into the incapacity of the immune system to efficiently control the bacterium, as well as reveal the power of the acquired immune system, wherein engagement of potent antigen-presentation early on may be sufficient to control an otherwise uncontrollable bacterium. The present results provide compelling evidence that modulation of the cell biology of antigen trafficking is a key avenue that is employed by various pathogens for immune evasion. The recombinant bacterium described herein may be used as a novel vaccine, wherein a key modification makes the bacterium generate rapid, potent CD8+ T cell response, resulting in self-destruction of the vaccine in vivo, making it highly efficacious, safe and cost-effective.

The utility of the recombinant bacterium described herein is demonstrated using OVA, TRP-2, and gp-100 as antigens. Using a similar approach, other putative antigens from other pathogens (bacteria, virus) or tumours can be cloned into the recombinant bacterium; these antigens can then be translocated into the host cell cytosol for rapid and potent antigen-presentation using the a translocation domain/chaperone system.

The present invention will be further illustrated in the following examples. However, it is to be understood that these examples are for illustrative purposes only and should not be used to limit the scope of the present invention in any manner.

Example 1

Preparation of Recombinant Bacteria

Recombinant bacteria comprising *Salmonella enterica*, serovar *Typhimurium* (ST) expressing ovalbumin (OVA) were prepared. Construct ST-OVA-NT, which does not translocate antigen to the cytosol, was prepared as previously described (Luu et al., 2006). A recombinant construct, ST-OVA-T, that produces an OVA fusion protein that is translocated to the cytosol; FIG. 1A shows a schematic of the fusion protein, where OVA is fused to YopE and SycE.

Figure 1B:
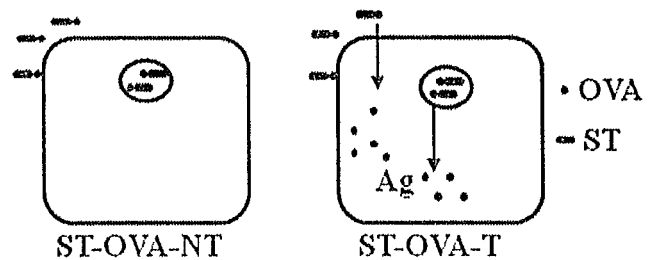
FIG. 1B shows a schematic of the antigen (OVA) translocation into the cytosol for ST-OVA-T, and the lack thereof for ST-OVA-NT. Ag: antigen; OVA: ovalbumin; ST: Salmonella Typhimurium.

YopE is a 23 kDa protein comprising a N-terminal secretion domain (~11 aa) and a translocation domain (at least 50 aa); the latter domain provides the binding site for the YopE-specific chaperone (SycE) that is required for YopE-mediated translocation of fused proteins to the cytosol (R). SycE is a chaperone necessary for translocation of the fused protein into the cytosol of infected cells through the type III secretion system of ST. A schematic of both ST-OVA-NT and ST-OVA-T constructs and their proposed actions are shown in FIG. 1B.

Plasmid pHR-OVA was constructed by the modification of the plasmid pHR-241 (Russmann et al., 2001), which contains the sequence of the fusion protein SycE-YopE-p60/M45 (Russmann et al., 2000). In a first step, the genes of p60/M45 were removed by cutting plasmid pHR-241 with BamHI and KpnI. Then, the pKK-OVA plasmid was purified from the recombinant ST-OVA-NT bacteria by mid prep kit (Invitrogen, US) according to the manufacturer's instructions. The OVA gene was PCR-amplified using the plasmid pKK-OVA as a template (forward primer BamHI 5'-CGGGATCCAACTTTCAAACAGCTG-3' (SEQ ID NO:13) and reverse primer KpnI 5'-GGGGTACCT-TAAGGGGAAACACATC-3' (SEQ ID NO:14). Subsequently, the OVA gene was inserted between the BamHI-KpnI sites of the cut pHR-241 plasmid, creating new plasmid pHR-OVA. PCR amplification of the inserts was performed with Taq polymerase using the following cycling parameters: 94° C., 5 min; 25 cycles of 94° C., 30 s to 58° C., 1 min to 72° C., 1 min; followed by a 7 min extension time at 72° C. The amplified insert was ligated into the intended vector then sequenced to verify the accuracy of the amplified cDNA. The pHR-OVA plasmid was then transfected into the highly virulent ST (strain SL1344). 50 μL of electrocompetent *Salmonella* (WT or aroA) were mixed with ~20 ng plasmid DNA and pulsed in a Bio-Rad micropulser using one pulse of 2.5 kV. Immediately afterwards, 1 mL of SOC recovery medium was added to the bacteria and they were allowed to recover with shaking at 37° C. The bacteria were then plated on LB agar plates with ampicillin for the selection of individual clones.

Example 2

Detection of Antigen

ST-OVA-NT and ST-OVA-T constructs of Example 1 were grown and expression and translocation of ovalbumin was evaluated. Pellet and supernatant of ST-OVA-NT and ST-OVA-T growing in liquid cultures were tested for the presence of OVA.

Figure 1C:
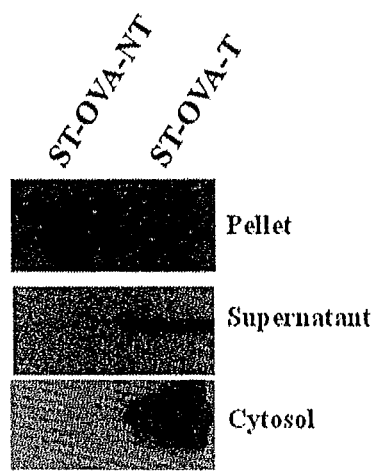
FIG. 1C shows expression of OVA (by western blot) in the bacterial pellet, supernatant, and the cytosol of spleen cells of mice infected for 24 h with ST-OVA-NT and ST-OVA-T.

C57BL/6J mice were injected intravenously with $10^6$ ST-OVA-NT or ST-OVA-T reconstituted in 200 microliters normal saline. Two days later, spleens were obtained from infected mice; spleen cells were isolated and lysed with TRITON X-100 in the presence of protease inhibitor, phenylmethylsulfonyl fluoride. The soluble lysate containing cytosolic proteins was tested for OVA expression by western blotting. Samples were normalized for cell number and were loaded on SDS-10% polyacrylamide gels. SDS-PAGE was performed and proteins were transferred to membranes, which were then blocked with 5% skim milk powder in PBS-TWEEN. OVA expression was detected using a 1/10,000 dilution of polyclonal anti-OVA antibody (Sigma-Aldrich), followed by incubation with HRP-conjugated goat anti-rabbit Ab (1/5,000 dilution in PBS-TWEEN) from Roche Applied Science. Immuno-reactive bands were detected with enhanced chemiluminescence substrate (Roche Applied Bioscience). Results show that OVA-expression by ST-OVA-NT and ST-OVA-T (from ~$5 \times 10^6$) in the bacterial pellets was similar (FIG. 1 C). However, OVA could only be detected in the supernatant of ST-OVA-T cultures. Expression of OVA was detectable in the cytosol of spleen cells from mice infected with ST-OVA-T- but not ST-OVA-NT (FIG. 1 C).

Example 3

Proliferation of ST-OVA-T and ST-OVA-NT

The ability of ST-OVA to proliferate extra- and intracellularly was also analyzed.

Figure 2A:
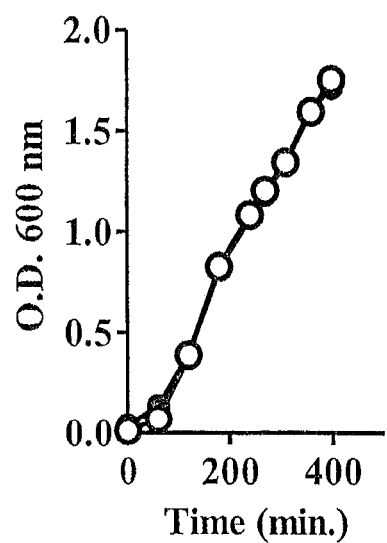

Liquid cultures of ST-OVA-NT and ST-OVA-T were set up in flasks to enumerate extracellular proliferation. At various time intervals (eg, 60 min., 120 min., 240 min., etc), aliquots were removed for measurement of OD at 600 nm. Both ST-OVA-NT and ST-OVA-T displayed similar proliferation and doubling time (FIG. 2A).

Figure 2B:
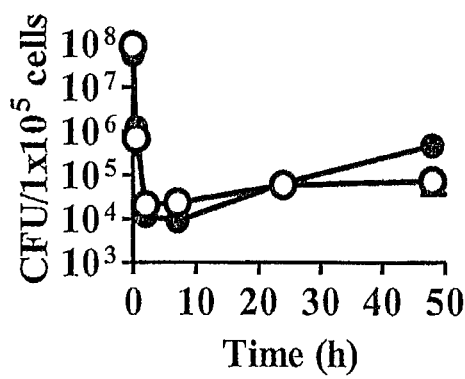
FIG. 2B is a graph showing the ST burden in IC-21 macrophages (H-$2^b$) infected with ST-OVA-NT or ST-OVA-T (multiplicity of infection, MOI=10). No statistically significant difference was detected in the ability of ST-OVA-NT or ST-OVA-T to infect and replicate within macrophages (p>0.05). Results are representative of three independent experiments.

The influence of antigenic translocation on the ability of ST-OVA to proliferate within the intracellular compartment was evaluated. IC-21 macrophages (H-$2^b$) ($5 \times 10^4$/well) were infected with ST-OVA-NT or ST-OVA-T (MOI=10). After 30 min, cells were washed and cultured in media containing gentamicin (50 μg/ml) to remove extracellular bacteria. After 2 h, cells were washed again and cultured in media containing reduced levels of gentamicin (10 μg/ml). At various time intervals cells were lysed and bacterial burden in the cells determined. No statistically significant difference was detected in the ability of ST-OVA-NT or ST-OVA-T to infect and replicate within macrophages (p>0.05). Results are shown in FIG. 2B and are representative of three independent experiments. Thus, the ability of ST-OVA to infect and survive within macrophages in vitro was not influenced by antigenic translocation.

Example 4

Translocation and Antigen Presentation

It was previously reported that ST-OVA-NT infection does not induce a detectable CD8$^+$ T cell response within the first week of infection (Luu et al., 2006), due to delayed presentation of antigen to CD8$^+$ T cells (Albaghdadi et al., 2009). Therefore, it was evaluated whether translocation of antigen to the cytosol would result in rapid antigen-presentation.

In vitro antigen-presentation was performed as previously described (Albaghdadi et al., 2009). IC-21 macrophages (H-$2^b$) cells ($10^5$/well) were infected with different MOI of ST (Albaghdadi et al., 2009), ST-OVA-NT (Example 1), or ST-OVA-T (Example 1) for 30 min. Extracellular bacteria were removed after incubation in medium containing gentamicin (50 μg/ml). At 2 h, cells were cultured in media containing lower levels of gentamicin (10 μg/ml) and incubated with CFSE-labelled OT-1 (CD45.1$^+$45.2$^-$) TCR transgenic cells ($10^6$/well). After 4 days of culture, cells were harvested, stained with anti-CD45.1 and anti-CD8 antibodies, and the reduction in CFSE intensity of OT-1 CD8$^+$ T cells was evaluated by flow cytometry.

Figure 3A:
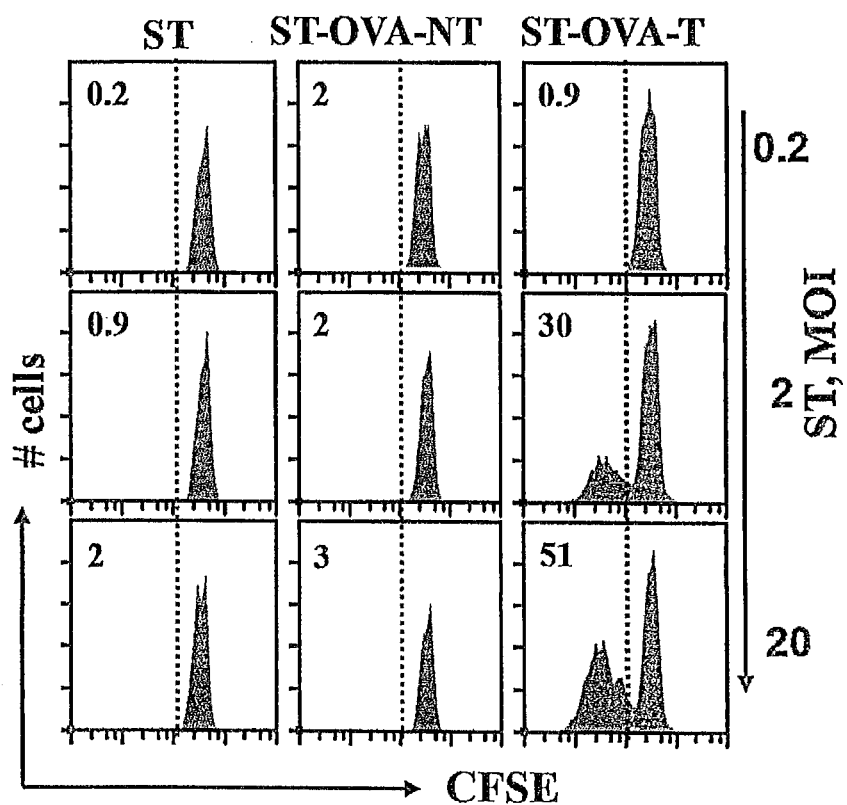
FIG. 3A shows flow cytometry results of in vitro infection of IC-21 macrophages (H-$2^b$) with recombinant bacteria (ST-OVA-NT, ST-OVA-T, or ST). The reduction in CFSE intensity of OT-1 CD8+ T cells indicated that infection of macrophages with ST or ST-OVA-NT did not result in any detectable proliferation of OT-1 cells, and thus, a lack of antigen-presentation. Infection with ST-OVA-T resulted in strong dilution of CFSE expression, which is indicative of rapid and potent antigen-presentation.

Infection of macrophages with ST or ST-OVA-NT did not result in any detectable proliferation of OT-1 cells, indicating lack of antigen-presentation (FIG. 3A). Interestingly, infection with ST-OVA-T, even at reduced doses, resulted in strong dilution of CFSE expression, which is indicative of rapid and potent antigen-presentation in vitro (FIG. 3A).

In vivo antigen-presentation was done as previously described (Albaghdadi et al., 2009). B6129F1 mice were infected with the recombinant bacteria of Example 1, followed by adoptive transfer of CFSE labelled OT-1 cells. B6.129F1 mice were used because B6 parents are highly susceptible and die within the first week of infection (Albaghdadi et al., 2009). Briefly, B6129F1 mice were generated in house by mating 129x1SvJ female mice with C57BL/6J male mice; mice were obtained from The Jackson Laboratory and were maintained at the Institute for Biological Sciences (National Research Council of Canada, Ottawa, Canada) in accordance with the guidelines of the Canadian Council on Animal Care. For immunization, frozen stocks of ST-OVA-NT or ST-OVA-T (Example 1) were thawed and diluted in 0.9% NaCl; mice were inoculated (iv) with $10^3$ organisms suspended in 200 µl. At various time intervals, CFSE-labelled OT-1 cells were injected ($5 \times 10^6$, iv). Four days after the transfer of OT-1 cells, spleens were isolated from recipient mice and spleen cells were stained with OVA-tetramer and anti-CD8 antibody. Reduction in the expression of CFSE intensity was evaluated by flow cytometry, as described above.

Figure 3B:
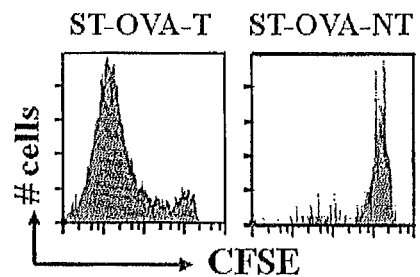
FIG. 3B shows flow cytometry results of in vivo infection of B6.129F1 mice infected with ST-OVA-NT or ST-OVA-T (Day 5). In ST-OVA-T-infected mice, the majority of transferred OT-1 cells displayed reduced expression of CFSE while OT-1 cells in ST-OVA-NT-infected mice maintained high levels of CFSE expression. Results represent the mean of three mice±SD per group, and are representative of 2-3 independent experiments.
Figure 3C:
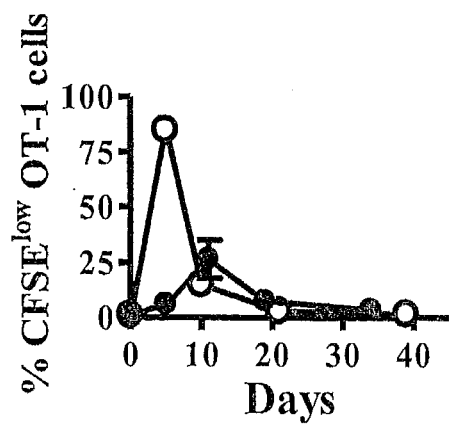
FIG. 3C is a graphical representation of the kinetic evaluation of in vivo antigen-presentation. ST-OVA-NT infected mice displayed muted and delayed activation of CFSE-labelled OT-1 cells. ST-OVA-NT (closed circles); ST-OVA-T (open circles).
Figure 4A:
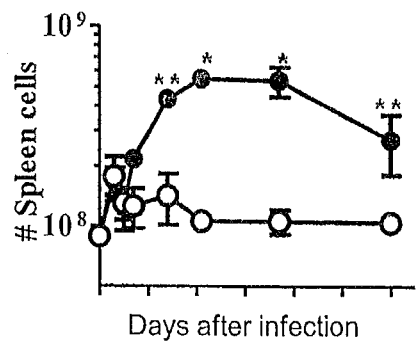
FIG. 4A shows the numbers of spleen cells, spleen size at Day 14 (FIG. 4B) and bacterial burden (FIG. 4C) in resistant (B6.129F1) mice infected with ST-OVA-T or ST-OVA-NT, as well as the percentage (FIG. 4D) and numbers (FIG. 4E) of OVA-specific CD8+ T cells in the spleen. Results represent the mean of three to five mice±SD per group and are representative of three independent experiments. ST-OVA-NT (closed circles); ST-OVA-T (open circles).
Figure 4B:
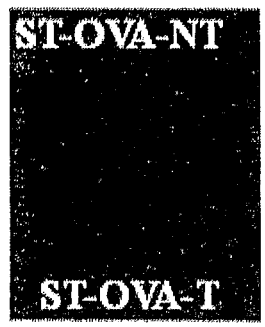
Figure 4C:
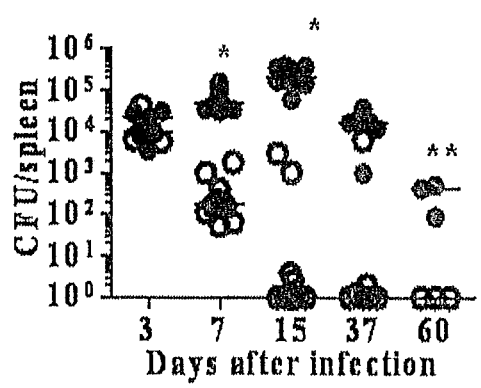
Figure 4D:
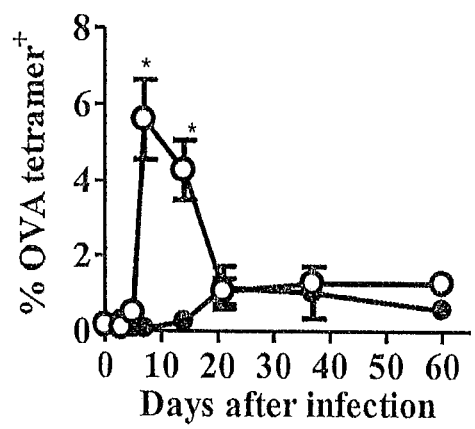
Figure 4E:
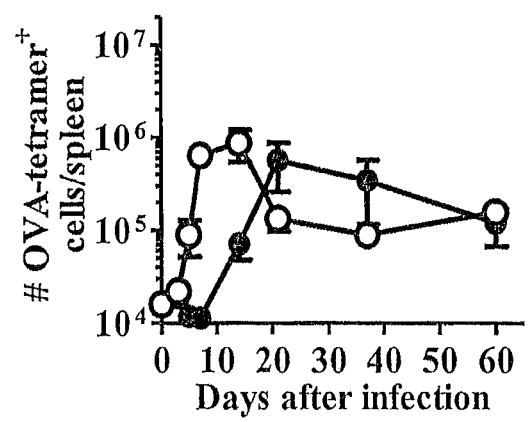

Results are shown in FIGS. 3B and 3C; results represent the mean of three mice±SD per group, and are representative of two-three independent experiments. At day 5 of infection, the majority of transferred OT-1 cells displayed reduced expression of CFSE in mice infected with ST-OVA-T (FIG. 3B). In contrast, OT-1 cells in ST-OVA-NT-infected mice maintained high levels of CFSE expression. When in vivo antigen-presentation was evaluated kinetically, ST-OVA-NT infected mice displayed muted and delayed activation of CFSE-labelled OT-1 cells (FIG. 3C). Interestingly, the massive antigen-presentation that was induced early on in ST-OVA-T infected mice was subsequently reduced to baseline levels as the pathogen was cleared.

Example 5

Antigen Translocation and CD8+ T Cell Response

The question of whether the induction of rapid antigen-presentation in vitro and in vivo by antigenic translocation to the cytosol would result in the development of a rapid CD8+ T cell response in vivo and whether this had any influence on pathogen control was examined.

B6.129F1 mice were infected ($10^3$, iv) with ST-OVA-T or ST-OVA-NT without any adoptive transfer of OT-1 cells. At various time intervals, the numbers of spleen cells, spleen size and bacterial burden were evaluated. OVA-specific CD8+ T cell response was enumerated by Flow cytometry. Briefly, aliquots of spleen cells ($5 \times 10^6$) were incubated in 80 µl of PBS plus 1% BSA (PBS-BSA) with anti-CD16/32 at 4° C. After 10 min., cells were stained with H-2K$^b$OVA$_{257-264}$ tetramer-PE (Beckman Coulter, US) and various antibodies (anti-CD8 PerCP-Cy5, anti-CD62L APC-Cy7, and anti-CD127 (PE-Cy7) for 30 min. All antibodies were obtained from BD Biosciences. Cells were washed with PBS, fixed in 0.5% formaldehyde and acquired on a BD Biosciences FACSCanto analyzer.

Figure 5A:
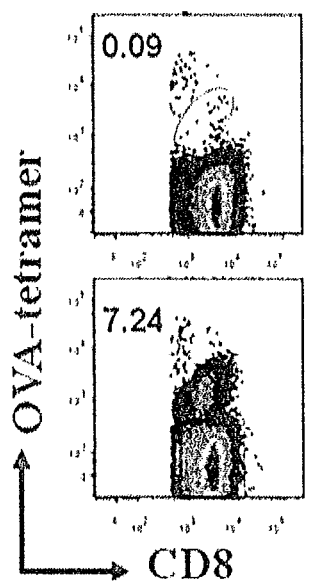
FIG. 5A shows the OVA-tetramer profile in the spleens of ST-OVA-T- or ST-OVA-NT-infected resistant (B6.129F1) mice at Day 7. The expression of CD62L (FIG. 5B, 5D) and CD127 (FIG. 5C, 5D) on OVA-tetramer+CD8+ T cells is also shown. Results are representative of three independent experiments. These results indicate early generation of memory CD8+ T cells in mice infected with ST-OVA-T. ST-OVA-NT (closed circles); ST-OVA-T (open circles).

Results are shown in FIG. 4; these results represent the mean of three to five mice±SD per group and are representative of three independent experiments. Infection of mice with ST-OVA-T resulted in the development of a rapid and potent OVA-specific CD8+ T cell response as evaluated by staining with OVA-tetramers (FIG. 4D, 4E; FIG. 5A); these mice displayed reduced spleen cell numbers and size (FIG. 4A, 4B). At day 3 of infection, similar bacterial burdens were noted in mice that received ST-OVA-T or ST-OVA-NT (FIG. 4C). However, at subsequent time intervals, the burden of ST-OVA-T were enormously controlled which was reduced to non-detectable levels by day 30. In contrast, ST-OVA-NT burden was maintained at high levels and the burden was detectable even at day 60 (FIG. 4C). Interestingly, at day 60, while both groups of mice had similar numbers of OVA-tetramer+ cells (FIG. 4E), the ST-OVA-T group of mice had controlled the burden whereas the ST-OVA-NT group of mice failed to control it (FIG. 4C); this suggests that direct antigen-presentation in case of ST-OVA-T makes the targets susceptible.

Figure 5B:
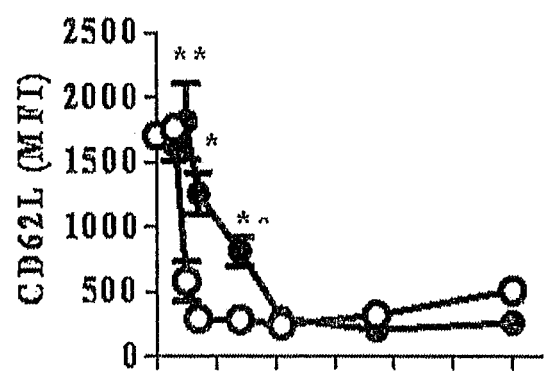
Figure 5C:
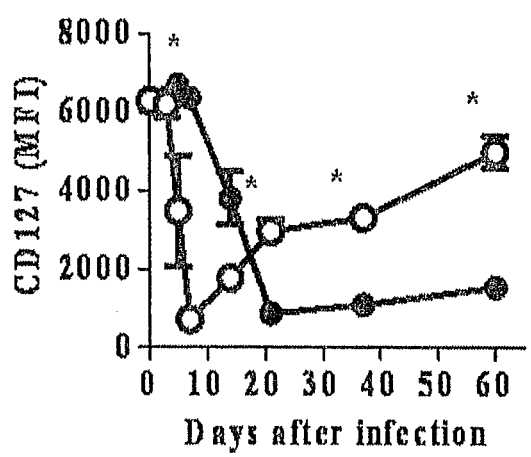
Figure 5D:
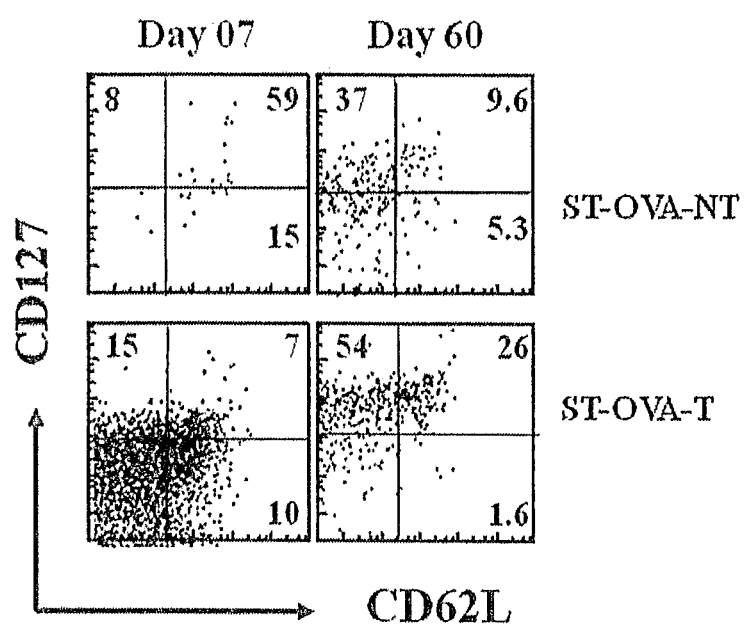

Phenotypic analysis of OVA-specific CD8+ T cells induced against ST-OVA-T versus ST-OVA-NT was also performed. FIG. 5A shows the OVA-tetramer profile in the spleens of infected mice, and the expression (MFI) of CD62L (FIG. 5B, 5D) and CD127 (FIG. 5C, 5D) on OVA-tetramer+CD8+ T cells. In contrast to ST-OVA-NT, OVA-specific CD8+ T cells induced against ST-OVA-T displayed rapid activation (CD62L down-regulation) and rapid progression to the memory state (CD127 up-regulation) (FIG. 5B-D). Taken together, these results clearly indicate that antigenic translocation to the cytosol in the context of ST infection accelerates the kinetics and increases the potency of antigen-presentation, CD8+ T cell differentiation, and memory development. Thus, the differentiation of CD8+ T cells that is noted with ST-OVA-T infection mirrors the one that is induced against the potent pathogen, LM.

Example 6

Rapid CD8+ T Cells Response and Survival of Susceptible Mice

Given the results noted with antigenic translocation in resistant mice (Example 5), determination of whether the rapid induction of CD8+ T cells would influence the survival of susceptible C57BL/6J mice was undertaken.

C57BL/6J mice were infected ($10^3$, iv) with ST-OVA-T or ST-OVA-NT. At different time points (day 1, 3, 5, 7 and 14) after infection, spleens were removed and the bacterial burdens were enumerated. Spleen cells were stained with OVA-tetramers and antibodies against CD8, CD62L and CD127. The percentage and numbers of OVA-specific CD8+ T cells were determined, as was the expression of CD62L versus CD127 on OVA-tetramer+CD8+ T cells.

Results are shown in FIG. 6 and represent the mean of three to four mice±SD per group; results are representative of two independent experiments. At days 1 and 3, similar bacterial burdens were noted in ST-OVA-NT- and ST-OIVA-T-infected groups (FIG. 6A). At later time periods, while the bacterial burden in ST-OVA-NT-infected mice continued to increase exponentially to lethal levels, the burden in ST-OVA-T-infected mice was rapidly controlled and became undetectable after day 14. Abridgment of bacterial burden in ST-OVA-T-infected mice correlated to the early emergence of potent OVA-specific CD8+ T cell response, as detected by OVA-tetramer staining (FIG. 6B-C) that peaked at day 7.

Example 7

Antigen Translocation Induces Functional CD8+ T Cells

Two functional assays were carried out to determine whether the CD8+ T cells that were induced by antigenic translocation would result in induction of CD8+ T cells that mediate appropriate functions.

Enumeration of IFN-γ secreting cells was performed by ELISPOT assay as reported previously at day 7 of infection (Dudani et al., 2002). ST-OVA-T-infected mice mounted a profound CD8$^+$ T cell response (FIG. 6D), indicative of IFN-γ production. In contrast, infection of susceptible mice with ST-OVA-NT did not result in any detectable IFN-γ-secreting CD8$^+$ T cells.

Figure 6A:
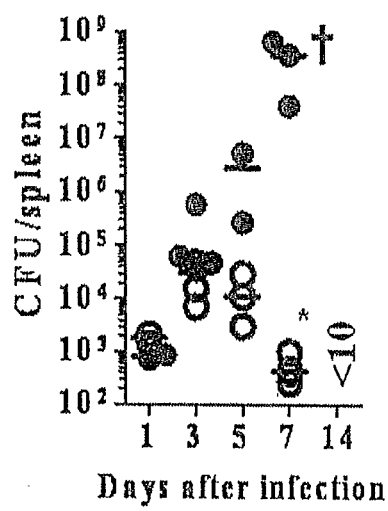
FIG. 6A shows the bacterial burdens in spleen cells of susceptible (C57BL/6J) mice infected with ST-OVA-T or ST-OVA-NT, along with the percentage (FIG. 6B) and numbers (FIG. 6C) of OVA-specific CD8+ T cells, as well as the frequency of OVA-specific CD8+ T cells evaluated by ELISPOT assay (FIG. 6D). The specific killing of OVA-pulsed targets in naïve mice exposed to OVA-pulsed and control spleen cells is shown if FIGS. 6E and F, indicating that ST-OVA-T infection results in rapid induction of antigen-specific CD8+ T cells that can efficiently kill antigen-bearing target cells. Results represent the mean of three to four mice±SD per group, and two independent experiments. ST-OVA-NT (closed circles); ST-OVA-T (open circles).
Figure 6B:
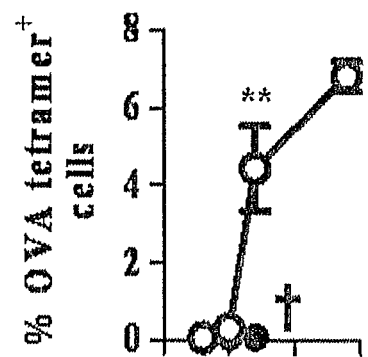
Figure 6C:
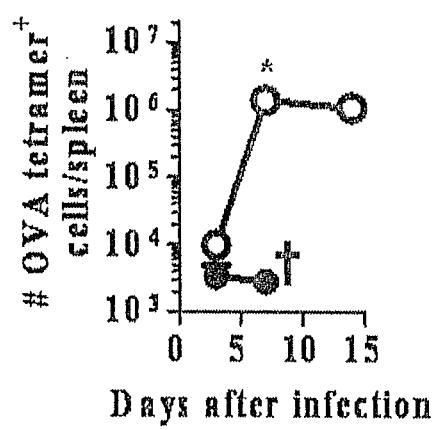
Figure 6D:
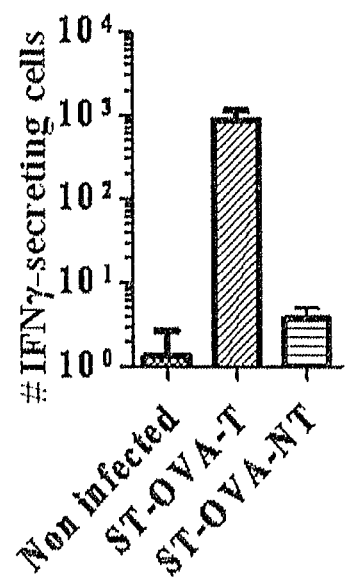
Figure 6E:
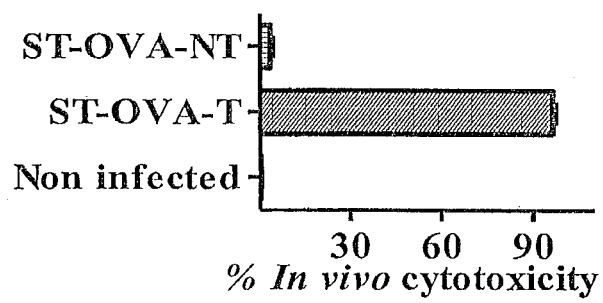
Figure 6F:
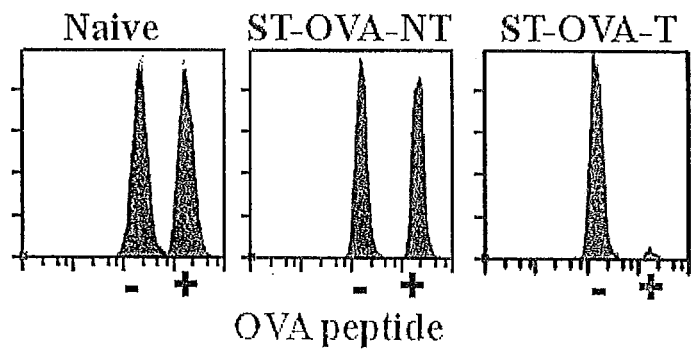

The ability of stimulated CD8$^+$ T cells to kill target cells specifically was enumerated as another functional readout. To do this, CFSE-labelled, OVA-pulsed and control spleen cells from naïve mice were transferred to ST-OVA-T- and ST-OVA-NT-infected mice on day 7, and the specific killing of OVA-pulsed targets was evaluated. In vivo cytolytic activity of CD8$^+$ T cells was performed according to previously published reports (Luu et al., 2006; Barber et al., 2003). OVA-specific CD8+ T cells that were induced at day 7 in ST-OVA-T-infected mice displayed rapid, potent and specific cytolytic activity towards OVA-pulsed target cells (FIG. 6E-F). In contrast, ST-OVA-NT-infected mice displayed little cytolytic activity, as expected (Luu et al., 2006). Thus, the kinetics of CD8+ T cells response in ST-OVA-T infected susceptible C57BL/6J was similar to that observed in resistant B6.129 F1 mice, as was their phenotype.

Figure 7A:
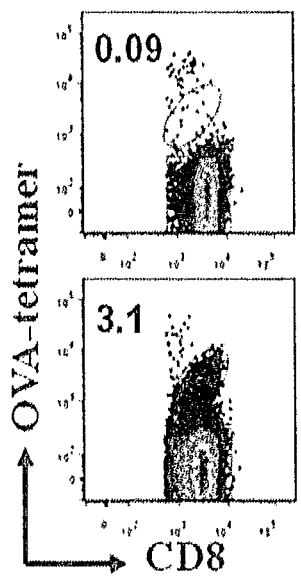
FIG. 7A shows the OVA-tetramer profile in the spleens of susceptible (C57BL/6J) mice infected with ST-OVA-T or ST-OVA-NT at Day 7.
Figure 7B:
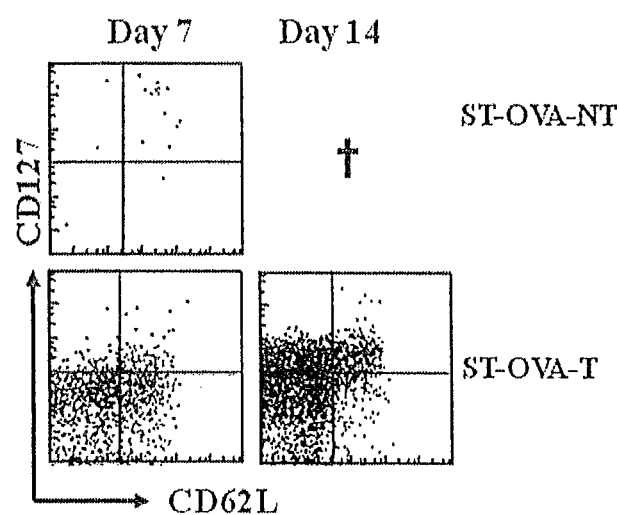
FIG. 7B shows the expression of CD62L versus CD127 on splenic OVA-tetramer+CD8+ T cells in the ST-OVA-T versus ST-OVA-NT infected mice. CD8+ T cells generated with ST-OVA-T infection express high levels of CD127 and CD62L (memory markers). Results are representative of three independent experiments.

FIG. 7 shows results of phenotypic analysis of OVA-specific CD8$^+$ T cells induced against ST-OVA-T versus ST-OVA-NT. Similar to the profile in resistant mice, OVA-specific CD8$^+$ T cells induced against ST-OVA-T in susceptible mice displayed rapid down-regulation of CD62L and rapid transition to the memory phenotype (increased CD127 up-regulation; FIG. 7).

Example 8

Control of Bacterial Growth

Figure 8A:
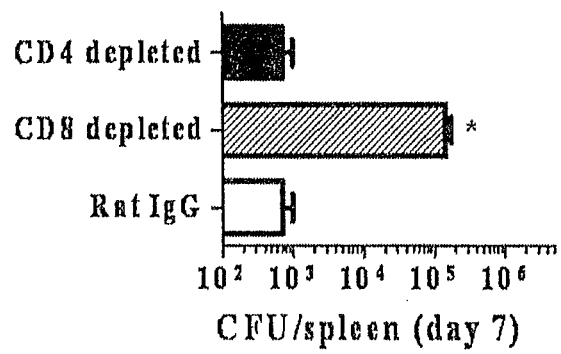
FIG. 8A shows the bacterial burden in spleens of C57BL/6J mice treated with anti-CD4 (clone GK1.5), anti-CD8 (clone 2.43) or Rat IgG isotype antibodies following infection with ST-OVA-T. Results represent the mean of three to four mice±SD per group. Anti-CD4 and anti-CD8 antibody treatment resulted in near complete elimination of CD4 and CD8+ T cells respectively.

While the data of Example 6 indicated that rapid emergence of functional CD8$^+$ T cells by antigenic translocation can control ST burden rapidly, it was still correlative. In order to test if the rapid emergence of CD8$^+$ T cells are responsible for elimination of bacteria during ST-OVA-T infection, C57BL/6J mice were treated with anti-CD8 or anti-CD4 antibody or isotype control then infected with ST-OVA-T to eliminate those cells specifically. C57BL/6J mice were treated with (100 μg/injection) anti-CD4 (clone GK1.5), anti-CD8 (clone 2.43), or Rat IgG isotype antibodies on days −3, 0 and 3 after infection with 10$^3$ ST-OVA-T. At day 7 after infection, spleens were harvested and the bacterial burden evaluated. At day 7 after infection, anti-CD8 antibody treated mice had a >100-fold higher ST-OVA-T burden (FIG. 8A), suggesting that when CD8$^+$ T cells are depleted, ST-OVA-T cannot be controlled by the host. Depletion of CD4$^+$ T cells had no effect on the bacterial burden.

Figure 8B:
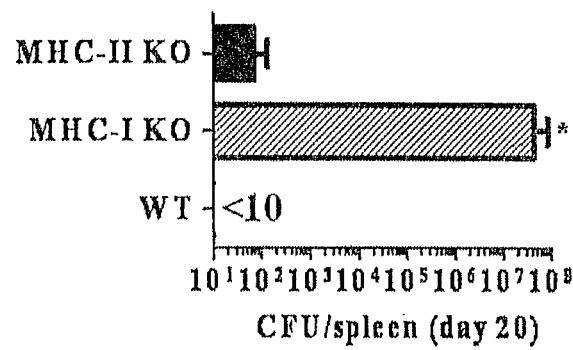
FIG. 8B shows the bacterial burden in spleens of WT, MHC-I- or MHC-II-deficient mice following infection with ST-OVA-T. These results indicate that the control of bacterial burden in ST-OVA-T infected mice is mediate exclusively by CD8+ T cells. Results represent the mean of five mice±SD per group.

The importance of CD8$^+$ T cells in controlling bacterial burden was further confirmed by infecting WT, MHC-I or MHC-II-deficient C57BL/6J mice with ST-OVA-T. Since MHC class I deficient mice lack CD8$^+$ T cells they should be susceptible to infection. Twenty days after infection, MHC-I deficient mice were moribund, displaying very high bacterial loads (FIG. 8B) whereas control mice had undetectable burden, and MHC class II-deficient hosts (lacking CD4$^+$ T cells) showed only a minor effect. MHC-I deficient mice were sick due to high bacterial loads, while MHC-II-deficient and WT mice were healthy. Taken together, these results indicate that antigenic translocation to cytosol in the context of ST infection results in a rapid emergence of a potent CD8$^+$ T cell response which is sufficient to control the burden.

Example 9

Translocation of Antigen in Attenuated Strain of *Salmonella*

In order to design vaccines, attenuated strains of bacteria are often used to avoid undesirable toxicity that occurs with highly virulent bacteria. It was therefore determined whether translocation of OVA in a highly attenuated strain of ST (ΔaroA) would induce rapid activation of CD8$^+$ T cells.

B6.129F1 mice were infected with 10$^3$ (virulent) wild type (WT; SL1344)) or 10$^5$ attenuated (avirulent; ΔaroA) ST-OVA expressing non-translocated or non-translocated OVA. At various time intervals (day 7, 14, 21 and 30), spleens and peripheral blood were collected and the relative change in the numbers of OVA-specific CD8$^+$ T cells enumerated after staining with OVA-tetramers and anti-CD8 antibodies as described in Example 5.

Figure 9A:
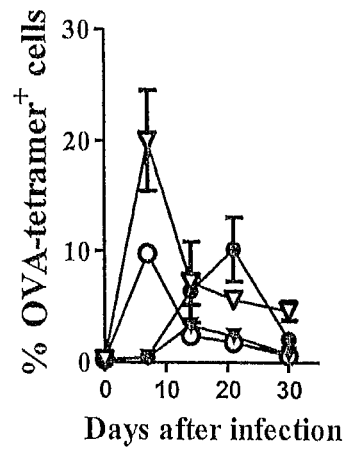
FIG. 9A shows the relative numbers of OVA-specific CD8+ T cells in the spleen and peripheral blood (FIG. 9B) of B6.129F1 mice infected with wild type (WT) or attenuated (ΔaroA) ST-OVA expressing non-translocated (NT) or translocated (T) OVA. Results represent the mean of five mice±SD per group. Results indicate that even attenuated strain of ST can induce potent and rapid CD8 T cell response when antigen is translocated to the cytosol of infected cells. WT-OVA-NT (closed circles); WT-OVA T (open circles); AroA-OVA-NT (closed inverted triangles); AroA-OVA-T (open inverted triangles).
Figure 9B:
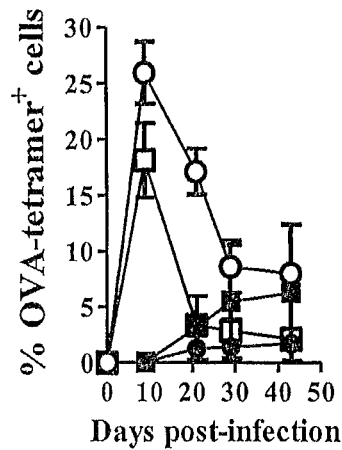

Results in FIG. 9 represent the mean of five mice±SD per group. Translocation of OVA by avirulent ST also resulted in rapid and profound induction of OVA-specific CD8$^+$ T cell response in the spleen (FIG. 9A) and peripheral blood (FIG. 9B). Thus, these results indicate that antigenic translocation works equally well for virulent and avirulent bacteria.

Example 10

Translocation of Antigen and Tumour Control

Figure 10A:
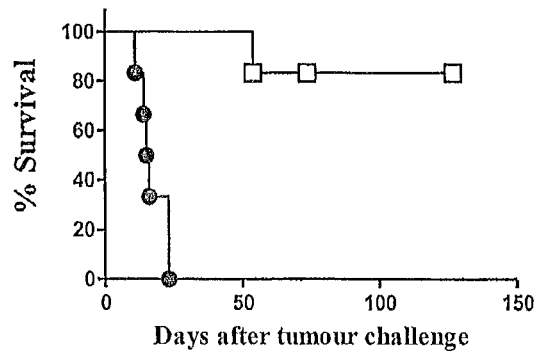
FIG. 10A is a graphical representation of the results of prophylactic vaccination with ST-OVA-T in C57BL/6J mice followed by subcutaneous challenge with B16-OVA tumor cells. This protocol resulted in potent protection against tumor challenge. Non-infected (closed circles); ST-OVA-T (open squares).
Figure 10B:
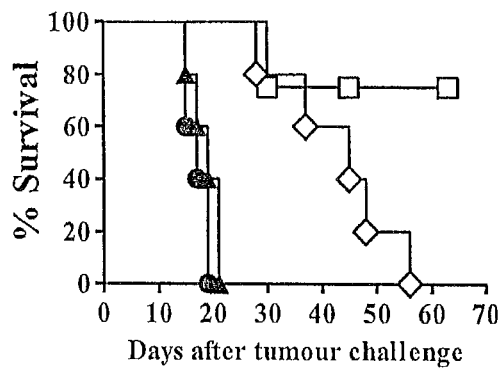
FIG. 10B shows a graph of results of therapeutic vaccination with ST-OVA-T in C57BL/6J mice after subcutaneous challenge with B16-OVA tumor cells. Mice receiving ST-OVA-T displayed the best protection against B16 melanoma cells. Protection induced by ST-OVA-T was far greater than that induced by ST-OVA-NT and the another recombinant bacterium, Listeria expressing OVA (LM-OVA). Results represent the mean of five mice±SD per group. Non-infected (full circles); ST-OVA-T (open squares); ST-OVA-NT (closed triangles); LM-OVA (open diamonds).

It was also investigated whether antigenic translocation would result in effective protection upon tumour challenge. C57BL/6J mice were infected with 10$^3$ ST-OVA-T; non-infected (naïve) mice served as controls. On day 60, mice were challenged subcutaneously in the lower dorsal region with 10$^6$ B16 melanoma cells carrying the OVA gene (B16-OVA). Survival of mice was measured subsequently. As shown in FIG. 10A, prophylactic vaccination with ST-OVA-T resulted in potent protection against tumour challenge. Protection in a therapeutic model, where mice were first challenged with tumours and then vaccinated with immunogens, was also tested. B6.129F1 mice were challenged first with 10$^6$ B16-OVA tumour cells subcutaneously in the lower dorsal region. Three days later, mice were vaccinated with ST-OVA-NT or ST-OVA-T. Non-infected mice served as negative controls and LM-OVA infected mice served as positive controls. At various time intervals subsequently, survival of mice was monitored. Mice receiving ST-OVA-T displayed the best protection against B16 melanoma cells (FIG. 10B). Protection induced by ST-OVA-T was far greater than that induced by ST-OVA-NT and LM-OVA. Results represent the mean of five mice±SD per group.

Example 11

CD8+ T Cell Response Against Tumor-Antigens

The use of OVA as an immunodominant antigen is described herein as a proof of principle. Using a similar approach, other putative antigens from other pathogens (bacteria, virus) or tumours can be cloned into ST and these antigens can be translocated into the host cell cytosol for rapid and potent antigen-presentation using the YopE/SycE system.

The gene for the tumour-antigen (Trp-2) (Schumacher and Restifo, 2009) was cloned into the WT or aroA mutant of ST, which translocates antigen to the cytosol. PCR was done using pCDNA3-Trp2 as template using the following primers:

```
                                              (SEQ ID NO: 15)
Forward primer: TAGGATCCGGAATTCTGCTCAGAG,
and (SEQ ID NO: 16)
Reverse primer: AGATGGTACCTTTAGTGCCACGTG.
```

The PCR product and pHR-OVA were digested with BamHI and KpnI and ligated. PCR amplification of the inserts was performed with Taq polymerase using the following cycling parameters: 94° C., 5 min; 25 cycles of 94° C., 30 s to 58° C., 1 min to 72° C., 1 min; followed by a 7 min extension time at 72° C. The amplified insert was ligated into the intended vector, then sequenced to verify the accuracy of the amplified cDNA. The PCR product was digested with BglII and KpnI; pHR-241 was digested with BamHI and KpnI and the digested products were ligated. pHR-Trp2 plasmid was then transfected into the highly virulent ST (SL1344) or aroA mutant of ST. 50 µL of electrocompetent *Salmonella* (WT or aroA) were mixed with ~20 ng plasmid DNA and pulsed in a Bio-Rad micropulser using one pulse of 2.5 kV. Immediately afterwards, 1 mL of SOC recovery medium was added to the bacteria and they were allowed to recover shaking at 37° C. The bacteria were then plated on LB agar plates with ampicillin for the selection of individual clones.

The gene for gp100 tumour-antigen (Rosenberg et al., 2008) was cloned into a pHR or pKK plasmid. PCR was done using pCDNA3-gp100 as template with the following primers:

```
                                              (SEQ ID NO: 17)
Forward primer: GAAGATCTGGGAAGAACACAATGG,
and (SEQ ID NO: 18)
Reverse primer: GGGGTACCTTAGGTGAGAGGAATGG.
```

Figure 11A:
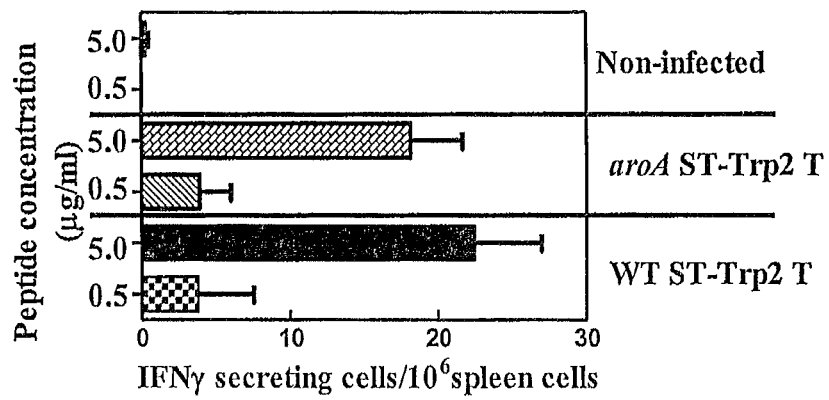
FIG. 11A shows the frequency of CD8+ T cells against a tumour antigen (Trp-2) in the spleens of mice infected with wild-type (WT) or attenuated (aroA) ST-Trp2-T on Day 7.
Figure 11B:
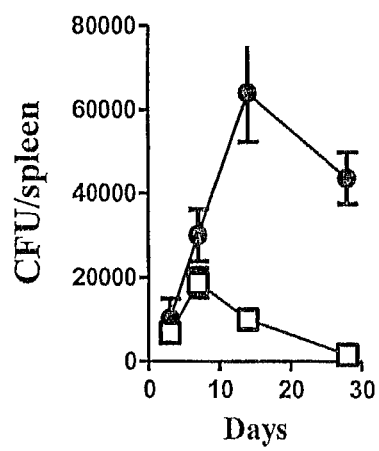
FIG. 11B shows the bacterial burden in the spleens of mice at various time intervals post-infection with WT ST-Trp2-T (open squares) or ST-Trp2-NT (closed circles).
Figure 11C:
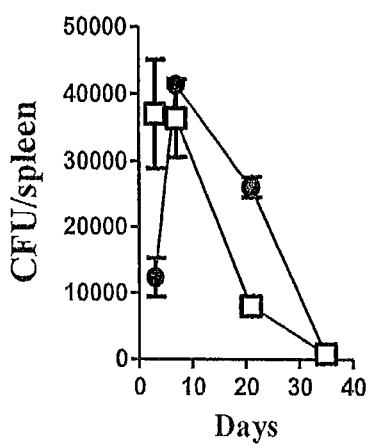
FIG. 11C shows the bacterial burden in the spleens of mice infected with aroA mutant of ST-Trp2-T (open squares) or NT (closed circles).
Figure 12A:
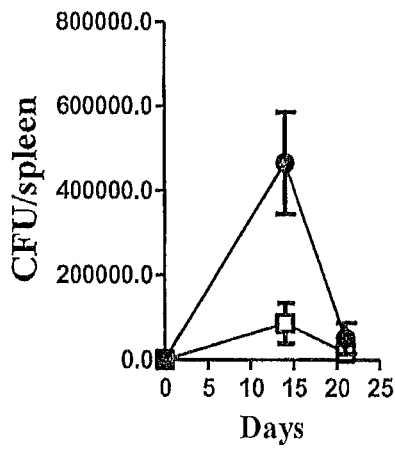
FIG. 12A shows the bacterial burden in the spleens of mice infected with translocated or non-translocated aroA-ST expressing another tumour antigen (gp100). aroA-gp100-T (open squares) or aroA-gp100-NT (closed circles).
Figure 12B:
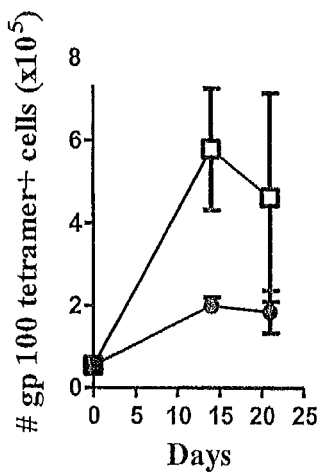
FIG. 12 B shows the numbers of gp100-tetramer+CD8+ T cells in the spleens of infected mice at various time intervals. aroA-ST-gp100-T (open squares); aroA-ST-gp100-NT (closed circles).

The PCR product was digested with BglII and KpnI; pHR-241 was digested with BamHI and KpnI and the digested products were ligated. Infection of B6.129F1 mice with these recombinant nucleic acids resulted in the induction of CD8+ T cell response against Trp-2 (FIG. 11A). This was associated with accelerated control of the bacterium (FIG. 11B,C). Similarly, infection of mice with the gp100 expressing aroA-ST resulted in accelerated control of the bacterium (FIG. 12A) and induction of a better CD8+ T cell response against gp100 (FIG. 12B).

Example 12

CD8+ T Cell Response to a Viral Antigen

The immunodominant epitope recognized to stimulate a CD8+ T cell response from LCMV nucleoprotein (NP) in C57Bl/6 mice was also used as an antigen and cloned into ST, and its effect on T cell response in mice was evaluated.

LCMV-NP was encoded over amino acids 396-404 (FQPQNGQFI—SEQ ID NO.: 25) of the protein (Basler et al., 2004). cDNA encoding amino acids 288-463 of the NP protein was cloned into plasmid pKK to generate pKK-NP (FIG. 13), using PCT methods as described in Example 1 and 11. Again, DH5 of, clones were selected using ampicillin. In this case, NcoI and NinaI restriction sites were added to the oligonucleotides used for amplification of the insert sequence. The oligonucleotide sequences used for the cDNA amplification were:

```
                                              (SEQ ID NO: 19)
5' TACCATGGCATTTGTTTCAGACCAAGT 3'
and (SEQ ID NO: 20)
5' TAAAGCTTCTAGTCCCTTACTATTCCAG 3'.
```

The final insert in the pKK plasmid was truncated prior to the end of the amplified insert due to the presence of an internal HindIII restriction site, ending at codon 461. After confirmation of the sequence, this plasmid was also transferred into ST wild type and STΔAro using a standard electroporation protocol (as described below and in Examples 1 and 11). cDNA encoding amino acids 288-461 of the NP protein was similarly cloned into the plasmid, pKK, to generate pKK-NP (FIG. 13). Again, DH5α clones were selected using ampicillin. In this case, NcoI and HindIII restriction sites were added to the oligonucleotides used for amplification of the insert sequence. The oligonucleotide sequences used for the cDNA amplification are:

```
                                              (SEQ ID NO: 21)
5' TACCATGGCATttgtttcagaccaaGT 3'
and (SEQ ID NO: 22)
5' TAAAGCTTCTAGTCCCTTACTATTCCAG 3'.
```

The final insert in the pKK plasmid was truncated prior to the end of the amplified insert due to the presence of an internal HindIII restriction site, ending at codon 461. After confirmation of the sequence, this plasmid was also transferred into ST wild type and STΔAro using a standard electroporation protocol. Briefly, 50 µL of electrocompetent *Salmonella* (WT or aroA) were mixed with ~20 ng plasmid DNA and pulsed in a Bio-Rad micropulser using one pulse of 2.5 kV. Immediately afterwards, 1 mL of SOC recovery medium was added to the bacteria and they were allowed to recover shaking at 37° C. The bacteria were then plated on LB agar plates with ampicillin for the selection of individual clones. PCR amplification of the inserts was performed with Taq polymerase using the following cycling parameters: 94° C., 5 min; 25 cycles of 94° C., 30 s to 58° C., 1 min to 72° C., 1 min; followed by a 7 min extension time at 72° C. The amplified insert was ligated into the intended vector then sequenced to verify the accuracy of the amplified cDNA.

Figure 13A:
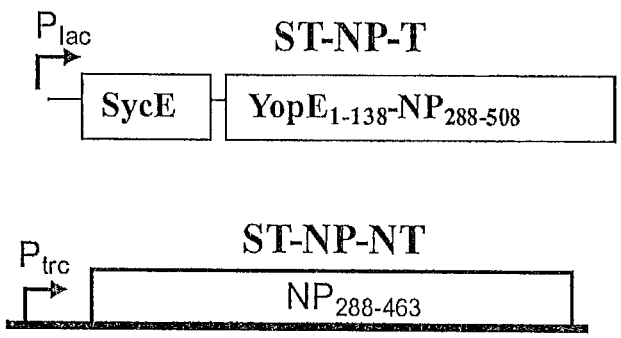
FIG. 13A shows the schematic of the fusion constructs.
Figure 13B:
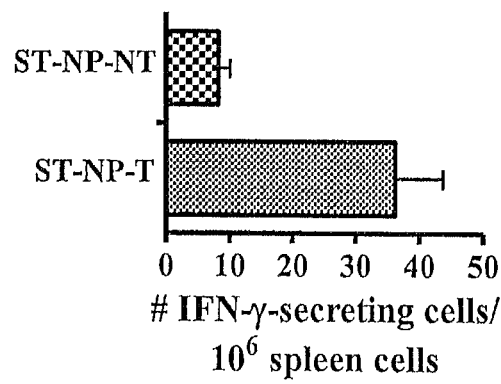
FIG. 13B shows the frequency of NP-specific CD8+ T cells in mice infected with ST-NP-T or ST-NP-NT at day 7 post-infection.
Figure 13C:
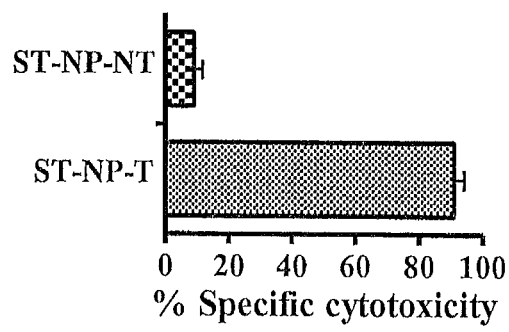
FIG. 13C shows the in vivo cytolytic activity of NP-specific CD8+ T cells on NP-pulsed target cells at day 7 post-infection. Cytolytic activity was evaluated after transferring naïve spleen cells (pulsed with media or NP peptide) into infected mice at day 7 and evaluated the killing of peptide-pulsed targets at 24 h post-transfer.
Figure 13D:
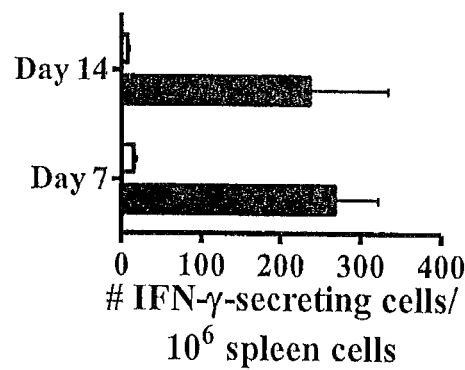
FIG. 13D shows the frequency of NP-specific CD8+ T cells in mice infected with aroA-NP-T (black bars) or aroA-NP-NT (white bars).
Figure 13E:
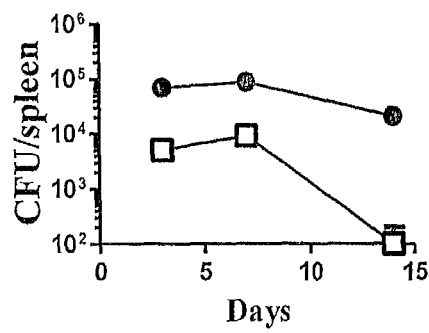
FIG. 13E shows the bacterial burden in the spleens at various time intervals. aroA-NP-T (open squares) or aroA-NP-NT (closed circles)
Figure 13F:
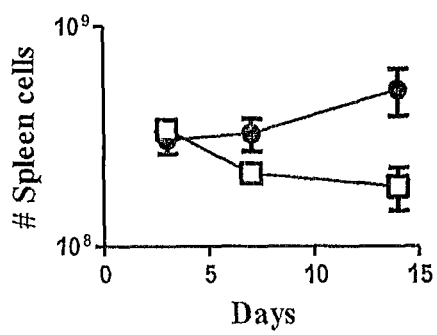
FIG. 13F shows the influence of antigenic translocation on the induction of inflammation in the spleen. aroA-NP-T (open squares); aroA-NP-NT (closed circles).

B6.129F1 mice were infected intravenously with $10^3$ recombinant ST expressing NP. Both virulent (FIG. 13B,C) and avirulent (FIG. 13D) ST induced profound NP-specific CD8+ T cell response when NP was translocated to the cytosol. Furthermore, antigenic translocation resulted in decreased bacterial burden (FIG. 13E) and control of vaccine induced inflammation (FIG. 13F).

Example 13

Use of Truncated YopE as a Means to Induce Potent CD8+ T Cell Response

Figure 14A:
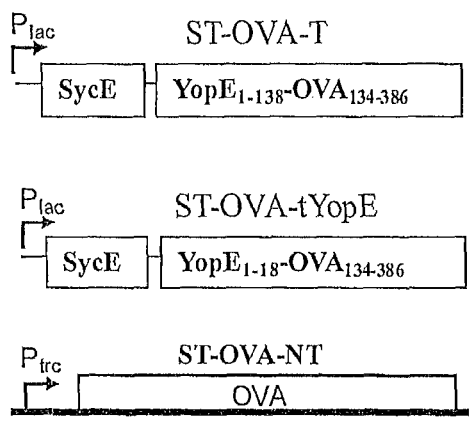
FIGS. 14A-14E shows that truncated YopE is equally effective at inducing CD8+ T cell response.

To determine whether the full length YopE was needed for induction of a better CD8+ T cell response, or whether a truncated version of this protein would be sufficient, the gene for OVA was fused with truncated YopE (first eighteen amino acids only), which does not carry the C-terminal domain for binding to the SycE chaperon (FIG. 14A). PCR was done using pHR-OVA as template with the following primers:

```
                                           (SEQ ID NO: 23)
Forward primer: GTGTCAAAGTTGGGGAATTCGC,
and
                                           (SEQ ID NO: 24)
Reverse primer: CTGCTGGATCCTGACACTGATG.
```

The PCR product and pHR-OVA were digested with EcoRI and BamHI and ligated. PCR amplification of the inserts was performed with Taq polymerase using the following cycling parameters: 94° C., 5 min; 25 cycles of 94° C., 30 s to 58° C., 1 min to 72° C., 1 min; followed by a 7 min extension time at 72° C. The amplified insert was ligated into the intended vector, then sequenced to verify the accuracy of the amplified cDNA.

Figure 14B:
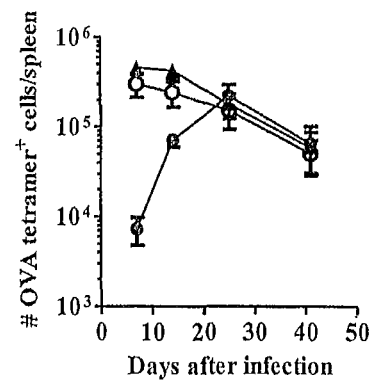
Figure 14C:
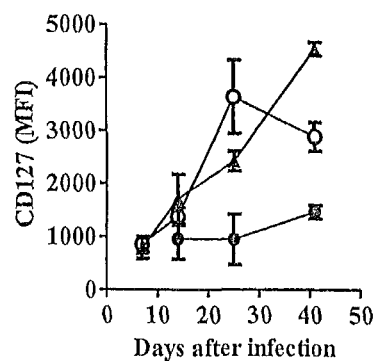
Figure 14D:
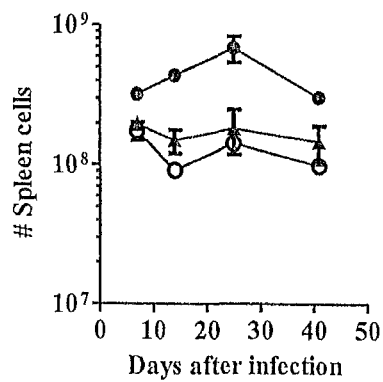
Figure 14E:
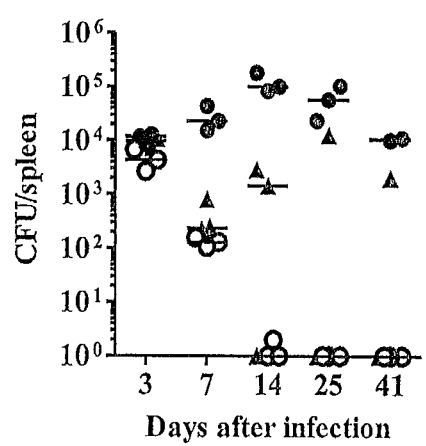

B6.129F1 mice were infected with ST-OVA-NT, ST-OVA-T (carrying full length YopE), and ST-OVA-tYopE (carrying truncated YopE). As is clear from results shown in FIG. 14B, the fusion of the desired antigen with the first eighteen amino acids of YopE is sufficient to induce rapid CD8+ T cell response. CD8+ T cells induced by the truncated YopE differentiated rapidly into memory cells (FIG. 14C), which lead to curtailment of inflammation (FIG. 14D) and bacterial burden (FIG. 14E).

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

All patents, patent applications and publications referred to herein and throughout the application are hereby incorporated by reference.

Albaghdadi, H., Robinson, N., Finlay, B., Krishnan, L., and Sad, S. (2009). Selectively reduced intracellular proliferation of Salmonella enterica serovar typhimurium within APCs limits antigen presentation and development of a rapid CD8 T cell response. J Immunol 183, 3778-3787.

Albert, M. L., Pearce, S. F., Francisco, L. M., Sauter, B., Roy, P., Silverstein, R. L., and Bhardwaj, N. (1998). Immature dendritic cells phagocytose apoptotic cells via alphavbeta5 and CD36, and cross-present antigens to cytotoxic T lymphocytes. J. Exp. Med. 188, 1359-1368.

Bahjat, K. S., Liu, W., Lemmens, E. E., Schoenberger, S. P., Portnoy, D. A., Dubensky, T. W., Jr., and Brockstedt, D. G. (2006). Cytosolic entry controls CD8+-T-cell potency during bacterial infection. Infect Immun 74, 6387-6397.

Barber, D. L., Wherry, E. J., and Ahmed, R. (2003). Cutting edge: rapid in vivo killing by memory CD8 T cells. J. Immunol. 171, 27-31.

Basler, M., Youhnovski, N., van den, B. M., Przybylski, M., and Groettrup, M. (2004). Immunoproteasomes down-regulate presentation of a subdominant T cell epitope from lymphocytic choriomeningitis virus. J Immunol 173, 3925-3934.

Bevan, M. J. (1995). Antigen presentation to cytotoxic T lymphocytes in vivo. J. Exp. Med. 182, 639-641.

Bliska, J. B., Galan, J. E., and Falkow, S. (1993). Signal transduction in the mammalian cell during bacterial attachment and entry. Cell 73, 903-920.

Dudani, R., Chapdelaine, Y., Faassen, H. H., Smith, D. K., Shen, H., Krishnan, L., and Sad, S. (2002). Multiple mechanisms compensate to enhance tumor-protective CD8(+) T cell response in the long-term despite poor CD8(+) T cell priming initially: comparison between an acute versus a chronic intracellular bacterium expressing a model antigen. J. Immunol. 168, 5737-5745.

Dudani, R., Murali-Krishna, K., Krishnan, L., and Sad, S. (2008). IFN-gamma induces the erosion of preexisting CD8 T cell memory during infection with a heterologous intracellular bacterium. J. Immunol. 181, 1700-1709.

Freigang, S., Egger, D., Bienz, K., Hengartner, H., and Zinkernagel, R. M. (2003). Endogenous neosynthesis vs. cross-presentation of viral antigens for cytotoxic T cell priming. Proc. Natl. Acad. Sci. U.S.A 100, 13477-13482.

Galan, J. E. and Curtiss, R., III (1989). Cloning and molecular characterization of genes whose products allow Salmonella typhimurium to penetrate tissue culture cells. Proc. Natl. Acad. Sci. U.S.A 86, 6383-6387.

Garvis, S. G., Beuzon, C. R., and Holden, D. W. (2001). A role for the PhoP/Q regulon in inhibition of fusion between lysosomes and Salmonella-containing vacuoles in macrophages. Cell Microbiol. 3, 731-744.

Groisman, E. A., Chiao, E., Lipps, C. J., and Heffron, F. (1989). Salmonella typhimurium phoP virulence gene is a transcriptional regulator. Proc. Natl. Acad. Sci. U.S.A 86, 7077-7081.

Hardt, W. D., Chen, L. M., Schuebel, K. E., Bustelo, X. R., and Galan, J. E. (1998). S. typhimurium encodes an activator of Rho GTPases that induces membrane ruffling and nuclear responses in host cells. Cell 93, 815-826.

Hensel, M., Shea, J. E., Gleeson, C., Jones, M. D., Dalton, E., and Holden, D. W. (1995). Simultaneous identification of bacterial virulence genes by negative selection. Science 269, 400-403.

Hersh, D., Monack, D. M., Smith, M. R., Ghori, N., Falkow, S., and Zychlinsky, A. (1999). The Salmonella invasin SipB induces macrophage apoptosis by binding to caspase-1. Proc. Natl. Acad. Sci. U.S.A 96, 2396-2401.

Hess, J. and Kaufmann, S. H. (1993). Vaccination strategies against intracellular microbes. FEMS Immunol. Med. Microbiol. 7, 95-103.

Hoiseth, S. K. and Stocker, B. A. (1981). Aromatic-dependent Salmonella typhimurium are non-virulent and effective as live vaccines. Nature 291, 238-239.

Houde, M., Bertholet, S., Gagnon, E., Brunet, S., Goyette, G., Laplante, A., Princiotta, M. F., Thibault, P., Sacks, D., and Desjardins, M. (2003). Phagosomes are competent organelles for antigen cross-presentation. Nature 425, 402-406.

Jones, B. D. and Falkow, S. (1996). Salmonellosis: host immune responses and bacterial virulence determinants. Annu. Rev. Immunol. 14, 533-561.

Kaech, S. M. and Ahmed, R. (2001). Memory CD8+ T cell differentiation: initial antigen encounter triggers a developmental program in naive cells. Nat. Immunol. 2, 415-422.

Kaech, S. M., Wherry, E. J., and Ahmed, R. (2002). Effector and memory T-cell differentiation: implications for vaccine development. Nat. Rev. Immunol. 2, 251-262.

Kaufmann, S. H. (1993). Immunity to intracellular bacteria. Annu. Rev. Immunol. 11, 129-163.

Kaufmann, S. H. and Hess, J. (1997). Rational design of antituberculosis vaccines: impact of antigen display and vaccine localization. Biologicals. 25, 169-173.

Kaufmann, S. H., Raupach, B., and Finlay, B. B. (2001). Introduction: microbiology and immunology: lessons learned from *Salmonella*. Microbes. Infect. 3, 1177-1181.

Krishnan, L., Sad, S., Patel, G. B., and Sprott, G. D. (2000). Archaeosomes induce long-term CD8+ cytotoxic T cell response to entrapped soluble protein by the exogenous cytosolic pathway, in the absence of CD4+ T cell help. J. Immunol. 165, 5177-5185.

Lee, S. H. and Galan, J. E. (2003). InvB is a type III secretion-associated chaperone for the *Salmonella enterica* effector protein SopE. J Bacteriol. 185, 7279-7284.

Luu, R. A., Gurnani, K., Dudani, R., Kammara, R., van Faassen, H., Sirard, J. C., Krishnan, L., and Sad, S. (2006). Delayed expansion and contraction of CD8+ T cell response during infection with virulent *Salmonella typhimurium*. J. Immunol. 177, 1516-1525.

Miller, S. I., Kukral, A. M., and Mekalanos, J. J. (1989). A two-component regulatory system (phoP phoQ) controls *Salmonella typhimurium* virulence. Proc. Natl. Acad. Sci. U.S.A 86, 5054-5058.

Moore, M. W., Carbone, F. R., and Bevan, M. J. (1988). Introduction of soluble protein into the class I pathway of antigen processing and presentation. Cell 54, 777-785.

Murali-Krishna, K., Altman, J. D., Suresh, M., Sourdive, D. J., Zajac, A. J., Miller, J. D., Slansky, J., and Ahmed, R. (1998). Counting antigen-specific CD8 T cells: a reevaluation of bystander activation during viral infection. Immunity. 8, 177-187.

Raupach, B. and Kaufmann, S. H. (2001). Bacterial virulence, proinflammatory cytokines and host immunity: how to choose the appropriate *Salmonella* vaccine strain? Microbes. Infect. 3, 1261-1269.

Rock, K. L. (1996). A new foreign policy: MHC class I molecules monitor the outside world. Immunol. Today 17, 131-137.

Rosenberg, S. A., Dudley, M. E., and Restifo, N. P. (2008). Cancer immunotherapy. N. Engl. J. Med. 359, 1072.

Russmann, H., Igwe, E. I., Sauer, J., Hardt, W. D., Bubert, A., and Geginat, G. (2001). Protection against murine listeriosis by oral vaccination with recombinant *Salmonella* expressing hybrid *Yersinia* type III proteins. J. Immunol. 167, 357-365.

Russmann, H., Shams, H., Poblete, F., Fu, Y., Galan, J. E., and Donis, R. O. (1998). Delivery of epitopes by the *Salmonella* type III secretion system for vaccine development. Science 281, 565-568.

Russmann, H., Weissmuller, A., Geginat, G., Igwe, E. I., Roggenkamp, A., Bubert, A., Goebel, W., Hof, H., and Heesemann, J. (2000). *Yersinia enterocolitica*-mediated translocation of defined fusion proteins to the cytosol of mammalian cells results in peptide-specific MHC class I-restricted antigen presentation. Eur. J. Immunol. 30, 1375-1384.

Schaible, U. E., Winau, F., Sieling, P. A., Fischer, K., Collins, H. L., Hagens, K., Modlin, R. L., Brinkmann, V., and Kaufmann, S. H. (2003). Apoptosis facilitates antigen presentation to T lymphocytes through MHC-I and CD1 in tuberculosis. Nat. Med. 9, 1039-1046.

Schumacher, T. N. and Restifo, N. P. (2009). Adoptive T cell therapy of cancer. Curr. Opin. Immunol. 21, 187-189.

Shea, J. E., Hensel, M., Gleeson, C., and Holden, D. W. (1996). Identification of a virulence locus encoding a second type III secretion system in *Salmonella typhimurium*. Proc. Natl. Acad. Sci. U.S.A 93, 2593-2597.

Smyth, M. J., Thia, K. Y., Street, S. E., MacGregor, D., Godfrey, D. I., and Trapani, J. A. (2000). Perforin-mediated cytotoxicity is critical for surveillance of spontaneous lymphoma. J. Exp. Med. 192, 755-760.

van der Velden, A. W., Lindgren, S. W., Worley, M. J., and Heffron, F. (2000). *Salmonella* pathogenicity island 1-independent induction of apoptosis in infected macrophages by *Salmonella enterica* serotype *typhimurium*. Infect. Immun. 68, 5702-5709.

Yrlid, U. and Wick, M. J. (2000). *Salmonella*-induced apoptosis of infected macrophages results in presentation of a bacteria-encoded antigen after uptake by bystander dendritic cells. J. Exp. Med. 191, 613-624.

Zhou, D. and Galan, J. (2001). *Salmonella* entry into host cells: the work in concert of type III secreted effector proteins. Microbes. Infect. 3, 1293-1298.

Zhu, X., Zhou, P., Cai, J., Yang, G., Liang, S., and Ren, D. (2010). Tumor antigen delivered by *Salmonella* III secretion protein fused with heat shock protein 70 induces protection and eradication against murine melanoma. Cancer Sci. 101, 2621-2628.

The invention claimed is:

1. A method of imparting immunity against a tumor, a bacterium, or a virus in a subject, the method comprising administering to said subject a recombinant *Salmonella* bacterium comprising a nucleic acid encoding a fusion protein comprising an antigen of the tumour, an antigen of the bacterium, or an antigen of the virus, and an N-terminal secretion signal from a type III secretion domain, wherein the N-terminal secretion signal consists of SEQ ID NO: 2, and wherein the method results in the translocation of the antigen to the cytosol of macrophages and/or dendritic cells of the subject leading to the activation of the antigen-specific CD8+ T cells in said subject.

2. The method of claim 1, wherein said administering is intravenous, oral, or subcutaneous.

3. The method of claim 1, wherein the fusion protein further comprises a chaperone.

4. The method of claim 3, wherein the chaperone is a component of a type III secretion system.

5. The method of claim 4, wherein the chaperone is SycE or HSP70.

6. The method of claim 1, wherein the nucleic acid is comprised in a vector.

7. The method claim 6, wherein the vector is a pHR vector.

8. The method of claim 6, wherein the vector is pHR-241.

9. The method of claim 1, wherein the tumour antigen is tyrosine-related protein 2 (TRP-2), MART-1, melanoma associated antigen 1 (MAGE1), Her-2/neu, or gp100.

* * * * *

SEQUENCE LISTING

```
<160> NUMBER OF SEQ ID NOS: 25

<210> SEQ ID NO 1
<211> LENGTH: 138
<212> TYPE: PRT
<213> ORGANISM: Artificial Sequence
<220> FEATURE:
<223> OTHER INFORMATION: Synthetic YopE

<400> SEQUENCE: 1

Met Lys Ile Ser Ser Phe Ile Ser Thr Ser Leu Pro Leu Pro Thr Ser
1               5                   10                  15

Val Ser Gly Ser Ser Ser Val Gly Glu Met Ser Gly Arg Ser Val Ser
            20                  25                  30

Gln Gln Lys Ser Glu Gln Tyr Ala Asn Asn Leu Ala Gly Arg Thr Glu
        35                  40                  45

Ser Pro Gln Gly Ser Ser Leu Ala Ser Arg Ile Thr Glu Lys Leu Ser
```

-continued

```
                50                  55                  60
Ser Met Ala Arg Ser Ala Ile Glu Phe Ile Lys Arg Met Phe Ser Glu
 65                  70                  75                  80

Gly Ser His Lys Pro Val Val Thr Pro Ala Pro Thr Pro Ala Gln Met
                 85                  90                  95

Pro Ser Pro Thr Ser Phe Ser Asp Ser Ile Lys Gln Leu Ala Ala Glu
                100                 105                 110

Thr Leu Pro Lys Tyr Ile Gln Gln Leu Ser Ser Leu Asp Ala Glu Thr
            115                 120                 125

Leu Gln Lys Asn His Asp Gln Phe Ala Thr
        130                 135

<210> SEQ ID NO 2
<211> LENGTH: 18
<212> TYPE: PRT
<213> ORGANISM: Artificial Sequence
<220> FEATURE:
<223> OTHER INFORMATION: Synthetic YopE fragment

<400> SEQUENCE: 2

Met Lys Ile Ser Ser Phe Ile Ser Thr Ser Leu Pro Leu Pro Thr Ser
 1               5                  10                  15

Val Ser

<210> SEQ ID NO 3
<211> LENGTH: 543
<212> TYPE: PRT
<213> ORGANISM: Artificial Sequence
<220> FEATURE:
<223> OTHER INFORMATION: Salmonella enterica SptP

<400> SEQUENCE: 3

Met Leu Lys Tyr Glu Glu Arg Lys Leu Asn Asn Leu Thr Leu Ser Ser
 1               5                  10                  15

Phe Ser Lys Val Gly Val Ser Asn Asp Ala Arg Leu Tyr Ile Ala Lys
                20                  25                  30

Glu Asn Thr Asp Lys Ala Tyr Val Ala Pro Glu Lys Phe Ser Ser Lys
            35                  40                  45

Val Leu Thr Trp Leu Gly Lys Met Pro Leu Phe Lys Asn Thr Glu Val
 50                  55                  60

Val Gln Lys His Thr Glu Asn Ile Arg Val Gln Asp Gln Lys Ile Leu
 65                  70                  75                  80

Gln Thr Phe Leu His Ala Leu Thr Glu Lys Tyr Gly Glu Thr Ala Val
                 85                  90                  95

Asn Asp Ala Leu Leu Met Ser Arg Ile Asn Met Asn Lys Pro Leu Thr
                100                 105                 110

Gln Arg Leu Ala Val Gln Ile Thr Glu Cys Val Lys Ala Ala Asp Glu
            115                 120                 125

Gly Phe Ile Asn Leu Ile Lys Ser Lys Asp Val Gly Val Arg Asn
        130                 135                 140

Ala Ala Leu Val Ile Lys Gly Gly Asp Thr Lys Val Ala Glu Lys Asn
145                 150                 155                 160

Asn Asp Val Gly Ala Glu Ser Lys Gln Pro Leu Leu Asp Ile Ala Leu
                165                 170                 175

Lys Gly Leu Lys Arg Thr Leu Pro Gln Leu Glu Gln Met Asp Gly Asn
            180                 185                 190

Ser Leu Arg Glu Asn Phe Gln Glu Met Ala Ser Gly Asn Gly Pro Leu
```

```
            195                 200                 205
Arg Ser Leu Met Thr Asn Leu Gln Asn Leu Asn Lys Ile Pro Glu Ala
    210                 215                 220

Lys Gln Leu Asn Asp Tyr Val Thr Thr Leu Thr Asn Ile Gln Val Gly
225                 230                 235                 240

Val Ala Arg Phe Ser Gln Trp Gly Thr Cys Gly Gly Glu Val Glu Arg
                245                 250                 255

Trp Val Asp Lys Ala Ser Thr His Glu Leu Thr Gln Ala Val Lys Lys
                260                 265                 270

Ile His Val Ile Ala Lys Glu Leu Lys Asn Val Thr Ala Glu Leu Glu
            275                 280                 285

Lys Ile Glu Ala Gly Ala Pro Met Pro Gln Thr Met Ser Gly Pro Thr
290                 295                 300

Leu Gly Leu Ala Arg Phe Ala Val Ser Ser Ile Pro Ile Asn Gln Gln
305                 310                 315                 320

Thr Gln Val Lys Leu Ser Asp Gly Met Pro Val Pro Val Asn Thr Leu
                325                 330                 335

Thr Phe Asp Gly Lys Pro Val Ala Leu Ala Gly Ser Tyr Pro Lys Asn
                340                 345                 350

Thr Pro Asp Ala Leu Glu Ala His Met Lys Met Leu Leu Glu Lys Glu
            355                 360                 365

Cys Ser Cys Leu Val Val Leu Thr Ser Glu Asp Gln Met Gln Ala Lys
370                 375                 380

Gln Leu Pro Pro Tyr Phe Arg Gly Ser Tyr Thr Phe Gly Glu Val His
385                 390                 395                 400

Thr Asn Ser Gln Lys Val Ser Ala Ser Gln Gly Glu Ala Ile Asp
                405                 410                 415

Gln Tyr Asn Met Gln Leu Ser Cys Gly Glu Lys Arg Tyr Thr Ile Pro
                420                 425                 430

Val Leu His Val Lys Asn Trp Pro Asp His Gln Pro Leu Pro Ser Thr
            435                 440                 445

Asp Gln Leu Glu Tyr Leu Ala Asp Arg Val Lys Asn Ser Asn Gln Asn
450                 455                 460

Gly Ala Pro Gly Arg Ser Ser Asp Lys His Leu Pro Met Ile His
465                 470                 475                 480

Cys Leu Gly Gly Val Gly Arg Thr Gly Thr Met Ala Ala Ala Leu Val
                485                 490                 495

Leu Lys Asp Asn Pro His Ser Asn Leu Glu Gln Val Arg Ala Asp Phe
                500                 505                 510

Arg Asp Ser Arg Asn Asn Arg Met Leu Glu Asp Ala Ser Gln Phe Val
            515                 520                 525

Gln Leu Lys Ala Met Gln Ala Gln Leu Leu Met Thr Thr Ala Ser
530                 535                 540

<210> SEQ ID NO 4
<211> LENGTH: 240
<212> TYPE: PRT
<213> ORGANISM: Artificial Sequence
<220> FEATURE:
<223> OTHER INFORMATION: Salmonella enterica SopE

<400> SEQUENCE: 4

Met Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
```

```
                    20                  25                  30
Lys Ser Ile Leu Ala Val Lys Asn His Phe Ile Glu Leu Arg Ser Lys
                35                  40                  45
Leu Ser Glu Arg Phe Ile Ser His Lys Asn Thr Glu Ser Ser Ala Thr
            50                  55                  60
His Phe His Arg Gly Ser Ala Ser Glu Gly Arg Ala Val Leu Thr Asn
 65                  70                  75                  80
Lys Val Val Lys Asp Phe Met Leu Gln Thr Leu Asn Asp Ile Asp Ile
                85                  90                  95
Arg Gly Ser Ala Ser Lys Asp Pro Ala Tyr Ala Ser Gln Thr Arg Glu
            100                 105                 110
Ala Ile Leu Ser Ala Val Tyr Ser Lys Asn Lys Asp Gln Cys Cys Asn
            115                 120                 125
Leu Leu Ile Ser Lys Gly Ile Asn Ile Ala Pro Phe Leu Gln Glu Ile
            130                 135                 140
Gly Glu Ala Ala Lys Asn Ala Gly Leu Pro Gly Thr Thr Lys Asn Asp
145                 150                 155                 160
Val Phe Thr Pro Ser Gly Ala Gly Ala Asn Pro Phe Ile Thr Pro Leu
                165                 170                 175
Ile Ser Ser Ala Asn Ser Lys Tyr Pro Arg Met Phe Ile Asn Gln His
            180                 185                 190
Gln Gln Ala Ser Phe Lys Ile Tyr Ala Glu Lys Ile Ile Met Thr Glu
            195                 200                 205
Val Ala Pro Leu Phe Asn Glu Cys Ala Met Pro Thr Pro Gln Gln Phe
            210                 215                 220
Gln Leu Ile Leu Glu Asn Ile Ala Asn Lys Tyr Ile Gln Asn Thr Pro
225                 230                 235                 240

<210> SEQ ID NO 5
<211> LENGTH: 130
<212> TYPE: PRT
<213> ORGANISM: Artificial Sequence
<220> FEATURE:
<223> OTHER INFORMATION: Synthetic SycE

<400> SEQUENCE: 5

Met Tyr Ser Phe Glu Gln Ala Ile Thr Gln Leu Phe Gln Gln Leu Ser
 1               5                  10                  15
Leu Ser Ile Pro Asp Thr Ile Glu Pro Val Ile Gly Val Lys Val Gly
                20                  25                  30
Glu Phe Ala Cys His Ile Thr Glu His Pro Val Gly Gln Ile Leu Met
            35                  40                  45
Phe Thr Leu Pro Ser Leu Asp Asn Asn Asn Glu Lys Glu Thr Leu Leu
         50                  55                  60
Ser His Asn Ile Phe Ser Gln Asp Ile Leu Lys Pro Ile Leu Ser Trp
 65                  70                  75                  80
Asp Glu Val Gly Gly His Pro Val Leu Trp Asn Arg Gln Pro Leu Asn
                85                  90                  95
Asn Leu Asp Asn Asn Ser Leu Tyr Thr Gln Leu Glu Met Leu Val Gln
            100                 105                 110
Gly Ala Glu Arg Leu Gln Thr Ser Ser Leu Ile Ser Pro Pro Arg Ser
            115                 120                 125
Phe Ser
130
```

-continued

```
<210> SEQ ID NO 6
<211> LENGTH: 638
<212> TYPE: PRT
<213> ORGANISM: Artificial Sequence
<220> FEATURE:
<223> OTHER INFORMATION: Salmonella enterica HSP70

<400> SEQUENCE: 6

Met Gly Lys Ile Ile Gly Ile Asp Leu Gly Thr Thr Asn Ser Cys Val
1               5                   10                  15

Ala Ile Met Asp Gly Thr Gln Ala Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Tyr Lys Ile Ile Gly Ala
                85                  90                  95

Asp Asn Gly Asp Ala Trp Leu Asp Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Glu Val Gly Asn Arg Thr Ile Ala Val
            180                 185                 190

Tyr Asp Leu Gly Gly Gly Thr Phe Asp Ile Ser Ile Ile Glu Ile Asp
        195                 200                 205

Glu Val Asp Gly Glu Lys Thr Phe Glu Val Leu Ala Thr Asn Gly Asp
    210                 215                 220

Thr His Leu Gly Gly Glu Asp Phe Asp Thr Arg Leu Ile Asn Tyr Leu
225                 230                 235                 240

Val Asp Glu Phe Lys Lys Asp Gln Gly Ile Asp Leu Arg Asn Asp Pro
                245                 250                 255

Leu Ala Met Gln Arg Leu Lys Glu Ala Ala Glu Lys Ala Lys Ile Glu
            260                 265                 270

Leu Ser Ser Ala Gln Gln Thr Asp Val Asn Leu Pro Tyr Ile Thr Ala
        275                 280                 285

Asp Ala Thr Gly Pro Lys His Met Asn Ile Lys Val Thr Arg Ala Lys
    290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asn Asp
                325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
        355                 360                 365

Glu Ala Val Ala Ile Gly Ala Ala Val Gln Gly Gly Val Leu Thr Gly
```

```
            370                 375                 380
Asp Val Lys Asp Val Leu Leu Asp Val Thr Pro Leu Ser Leu Gly
385                 390                 395                 400

Ile Glu Thr Met Gly Gly Val Met Thr Pro Leu Ile Thr Lys Asn Thr
                405                 410                 415

Thr Ile Pro Thr Lys His Ser Gln Val Phe Ser Thr Ala Glu Asp Asn
            420                 425                 430

Gln Ser Ala Val Thr Ile His Val Leu Gln Gly Glu Arg Lys Arg Ala
        435                 440                 445

Ser Asp Asn Lys Ser Leu Gly Gln Phe Asn Leu Asp Gly Ile Asn Pro
    450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
                485                 490                 495

Gln Lys Ile Thr Ile Lys Ala Ser Ser Gly Leu Asn Glu Glu Glu Ile
                500                 505                 510

Gln Lys Met Val Arg Asp Ala Glu Ala Asn Ala Glu Ser Asp Arg Lys
            515                 520                 525

Phe Glu Glu Leu Val Gln Thr Arg Asn Gln Gly Asp His Leu Leu His
530                 535                 540

Ser Thr Arg Lys Gln Val Glu Glu Ala Gly Asp Lys Leu Pro Ala Asp
545                 550                 555                 560

Asp Lys Thr Ala Ile Glu Ser Ala Leu Asn Ala Leu Glu Thr Ala Leu
                565                 570                 575

Lys Gly Glu Asp Lys Ala Ala Ile Glu Ala Lys Met Gln Glu Leu Ala
                580                 585                 590

Gln Val Ser Gln Lys Leu Met Glu Ile Ala Gln Gln His Ala Gln
            595                 600                 605

Gln Gln Ala Gly Ser Ala Asp Ala Ser Ala Asn Asn Ala Lys Asp Asp
        610                 615                 620

Asp Val Val Asp Ala Glu Phe Glu Glu Val Lys Asp Lys Lys
625                 630                 635

<210> SEQ ID NO 7
<211> LENGTH: 523
<212> TYPE: PRT
<213> ORGANISM: Artificial Sequence
<220> FEATURE:
<223> OTHER INFORMATION: Synthetic SycE-YopE-OVA

<400> SEQUENCE: 7

Met Tyr Ser Phe Glu Gln Ala Ile Thr Gln Leu Phe Gln Gln Leu Ser
1               5                   10                  15

Leu Ser Ile Pro Asp Thr Ile Glu Pro Val Ile Gly Val Lys Val Gly
            20                  25                  30

Glu Phe Ala Cys His Ile Thr Glu His Pro Val Gly Gln Ile Leu Met
        35                  40                  45

Phe Thr Leu Pro Ser Leu Asp Asn Asn Asn Glu Lys Glu Thr Leu Leu
    50                  55                  60

Ser His Asn Ile Phe Ser Gln Asp Ile Leu Lys Pro Ile Leu Ser Trp
65                  70                  75                  80

Asp Glu Val Gly Gly His Pro Val Leu Trp Asn Arg Gln Pro Leu Asn
                85                  90                  95

Asn Leu Asp Asn Asn Ser Leu Tyr Thr Gln Leu Glu Met Leu Val Gln
```

```
            100                 105                 110
Gly Ala Glu Arg Leu Gln Thr Ser Ser Leu Ile Ser Pro Pro Arg Ser
            115                 120                 125

Phe Ser Met Lys Ile Ser Ser Phe Ile Ser Thr Ser Leu Pro Leu Pro
            130                 135                 140

Thr Ser Val Ser Gly Ser Ser Val Gly Glu Met Ser Gly Arg Ser
145                 150                 155                 160

Val Ser Gln Gln Lys Ser Glu Gln Tyr Ala Asn Asn Leu Ala Gly Arg
            165                 170                 175

Thr Glu Ser Pro Gln Gly Ser Ser Leu Ala Ser Arg Ile Thr Glu Lys
            180                 185                 190

Leu Ser Ser Met Ala Arg Ser Ala Ile Glu Phe Ile Lys Arg Met Phe
            195                 200                 205

Ser Glu Gly Ser His Lys Pro Val Val Thr Pro Ala Pro Thr Pro Ala
            210                 215                 220

Gln Met Pro Ser Pro Thr Ser Phe Ser Asp Ser Ile Lys Gln Leu Ala
225                 230                 235                 240

Ala Glu Thr Leu Pro Lys Tyr Ile Gln Gln Leu Ser Ser Leu Asp Ala
            245                 250                 255

Glu Thr Leu Gln Lys Asn His Asp Gln Phe Ala Thr Gly Ser Asn Phe
            260                 265                 270

Gln Thr Ala Ala Asp Gln Ala Arg Glu Leu Ile Asn Ser Arg Val Glu
            275                 280                 285

Ser Gln Thr Asn Gly Ile Ile Arg Asn Val Leu Gln Pro Ser Ser Val
            290                 295                 300

Asp Ser Gln Thr Ala Met Val Leu Val Asn Ala Ile Val Phe Lys Gly
305                 310                 315                 320

Leu Trp Glu Lys Ala Phe Lys Asp Glu Asp Thr Gln Ala Met Pro Phe
            325                 330                 335

Arg Val Thr Glu Gln Glu Ser Lys Pro Val Gln Met Met Tyr Gln Ile
            340                 345                 350

Gly Leu Phe Arg Val Ala Ser Met Ala Ser Glu Lys Met Lys Ile Leu
            355                 360                 365

Glu Leu Pro Phe Ala Ser Gly Thr Met Ser Met Leu Val Leu Leu Pro
            370                 375                 380

Asp Glu Val Ser Gly Leu Glu Gln Leu Glu Ser Ile Ile Asn Phe Glu
385                 390                 395                 400

Lys Leu Thr Glu Trp Thr Ser Ser Asn Val Met Glu Glu Arg Lys Ile
            405                 410                 415

Lys Val Tyr Leu Pro Arg Met Lys Met Glu Glu Lys Tyr Asn Leu Thr
            420                 425                 430

Ser Val Leu Met Ala Met Gly Ile Thr Asp Val Phe Ser Ser Ser Ala
            435                 440                 445

Asn Leu Ser Gly Ile Ser Ser Ala Glu Ser Leu Lys Ile Ser Gln Ala
            450                 455                 460

Val His Ala Ala His Ala Glu Ile Asn Glu Ala Gly Arg Glu Val Val
465                 470                 475                 480

Gly Ser Ala Glu Ala Gly Val Asp Ala Ala Ser Val Ser Glu Glu Phe
            485                 490                 495

Arg Ala Asp His Pro Phe Leu Phe Cys Ile Lys His Ile Ala Thr Asn
            500                 505                 510

Ala Val Leu Phe Phe Gly Arg Cys Val Ser Pro
            515                 520
```

-continued

<210> SEQ ID NO 8
<211> LENGTH: 403
<212> TYPE: PRT
<213> ORGANISM: Artificial Sequence
<220> FEATURE:
<223> OTHER INFORMATION: Synthetic SycE-YopE(18)-OVA

<400> SEQUENCE: 8

```
Met Tyr Ser Phe Glu Gln Ala Ile Thr Gln Leu Phe Gln Gln Leu Ser
1               5                   10                  15

Leu Ser Ile Pro Asp Thr Ile Glu Pro Val Ile Gly Val Lys Val Gly
            20                  25                  30

Glu Phe Ala Cys His Ile Thr Glu His Pro Val Gly Gln Ile Leu Met
        35                  40                  45

Phe Thr Leu Pro Ser Leu Asp Asn Asn Asn Glu Lys Glu Thr Leu Leu
    50                  55                  60

Ser His Asn Ile Phe Ser Gln Asp Ile Leu Lys Pro Ile Leu Ser Trp
65                  70                  75                  80

Asp Glu Val Gly Gly His Pro Val Leu Trp Asn Arg Gln Pro Leu Asn
                85                  90                  95

Asn Leu Asp Asn Asn Ser Leu Tyr Thr Gln Leu Glu Met Leu Val Gln
            100                 105                 110

Gly Ala Glu Arg Leu Gln Thr Ser Ser Leu Ile Ser Pro Pro Arg Ser
        115                 120                 125

Phe Ser Met Lys Ile Ser Ser Phe Ile Ser Thr Ser Leu Pro Leu Pro
    130                 135                 140

Thr Ser Val Ser Gly Ser Asn Phe Gln Thr Ala Ala Asp Gln Ala Arg
145                 150                 155                 160

Glu Leu Ile Asn Ser Arg Val Glu Ser Gln Thr Asn Gly Ile Ile Arg
                165                 170                 175

Asn Val Leu Gln Pro Ser Ser Val Asp Ser Gln Thr Ala Met Val Leu
            180                 185                 190

Val Asn Ala Ile Val Phe Lys Gly Leu Trp Glu Lys Ala Phe Lys Asp
        195                 200                 205

Glu Asp Thr Gln Ala Met Pro Phe Arg Val Thr Glu Gln Glu Ser Lys
    210                 215                 220

Pro Val Gln Met Met Tyr Gln Ile Gly Leu Phe Arg Val Ala Ser Met
225                 230                 235                 240

Ala Ser Glu Lys Met Lys Ile Leu Glu Leu Pro Phe Ala Ser Gly Thr
                245                 250                 255

Met Ser Met Leu Val Leu Leu Pro Asp Glu Val Ser Gly Leu Glu Gln
            260                 265                 270

Leu Glu Ser Ile Ile Asn Phe Glu Lys Leu Thr Glu Trp Thr Ser Ser
        275                 280                 285

Asn Val Met Glu Glu Arg Lys Ile Lys Val Tyr Leu Pro Arg Met Lys
    290                 295                 300

Met Glu Glu Lys Tyr Asn Leu Thr Ser Val Leu Met Ala Met Gly Ile
305                 310                 315                 320

Thr Asp Val Phe Ser Ser Ala Asn Leu Ser Gly Ile Ser Ser Ala
                325                 330                 335

Glu Ser Leu Lys Ile Ser Gln Ala Val His Ala Ala His Ala Glu Ile
            340                 345                 350

Asn Glu Ala Gly Arg Glu Val Val Gly Ser Ala Glu Ala Gly Val Asp
        355                 360                 365
```

```
Ala Ala Ser Val Ser Glu Glu Phe Arg Ala Asp His Pro Phe Leu Phe
        370                 375                 380
Cys Ile Lys His Ile Ala Thr Asn Ala Val Leu Phe Phe Gly Arg Cys
385                 390                 395                 400
Val Ser Pro

<210> SEQ ID NO 9
<211> LENGTH: 273
<212> TYPE: PRT
<213> ORGANISM: Artificial Sequence
<220> FEATURE:
<223> OTHER INFORMATION: Synthetic YopE(18)-OVA

<400> SEQUENCE: 9

Met Lys Ile Ser Ser Phe Ile Ser Thr Ser Leu Pro Leu Pro Thr Ser
1               5                   10                  15
Val Ser Gly Ser Asn Phe Gln Thr Ala Ala Asp Gln Ala Arg Glu Leu
            20                  25                  30
Ile Asn Ser Arg Val Glu Ser Gln Thr Asn Gly Ile Ile Arg Asn Val
        35                  40                  45
Leu Gln Pro Ser Ser Val Asp Ser Gln Thr Ala Met Val Leu Val Asn
    50                  55                  60
Ala Ile Val Phe Lys Gly Leu Trp Glu Lys Ala Phe Lys Asp Glu Asp
65                  70                  75                  80
Thr Gln Ala Met Pro Phe Arg Val Thr Glu Gln Glu Ser Lys Pro Val
                85                  90                  95
Gln Met Met Tyr Gln Ile Gly Leu Phe Arg Val Ala Ser Met Ala Ser
            100                 105                 110
Glu Lys Met Lys Ile Leu Glu Leu Pro Phe Ala Ser Gly Thr Met Ser
        115                 120                 125
Met Leu Val Leu Leu Pro Asp Glu Val Ser Gly Leu Glu Gln Leu Glu
    130                 135                 140
Ser Ile Ile Asn Phe Glu Lys Leu Thr Glu Trp Thr Ser Ser Asn Val
145                 150                 155                 160
Met Glu Glu Arg Lys Ile Lys Val Tyr Leu Pro Arg Met Lys Met Glu
                165                 170                 175
Glu Lys Tyr Asn Leu Thr Ser Val Leu Met Ala Met Gly Ile Thr Asp
            180                 185                 190
Val Phe Ser Ser Ser Ala Asn Leu Ser Gly Ile Ser Ser Ala Glu Ser
        195                 200                 205
Leu Lys Ile Ser Gln Ala Val His Ala Ala His Ala Glu Ile Asn Glu
    210                 215                 220
Ala Gly Arg Glu Val Val Gly Ser Ala Glu Ala Gly Val Asp Ala Ala
225                 230                 235                 240
Ser Val Ser Glu Glu Phe Arg Ala Asp His Pro Phe Leu Phe Cys Ile
                245                 250                 255
Lys His Ile Ala Thr Asn Ala Val Leu Phe Phe Gly Arg Cys Val Ser
            260                 265                 270
Pro

<210> SEQ ID NO 10
<211> LENGTH: 613
<212> TYPE: PRT
<213> ORGANISM: Artificial Sequence
<220> FEATURE:
<223> OTHER INFORMATION: Synthetic SycE-YopE-Trp2
```

<400> SEQUENCE: 10

```
Met Tyr Ser Phe Glu Gln Ala Ile Thr Gln Leu Phe Gln Gln Leu Ser
1               5                   10                  15

Leu Ser Ile Pro Asp Thr Ile Glu Pro Val Ile Gly Val Lys Val Gly
            20                  25                  30

Glu Phe Ala Cys His Ile Thr Glu His Pro Val Gly Gln Ile Leu Met
        35                  40                  45

Phe Thr Leu Pro Ser Leu Asp Asn Asn Glu Lys Glu Thr Leu Leu
    50                  55                  60

Ser His Asn Ile Phe Ser Gln Asp Ile Leu Lys Pro Ile Leu Ser Trp
65                  70                  75                  80

Asp Glu Val Gly Gly His Pro Val Leu Trp Asn Arg Gln Pro Leu Asn
                85                  90                  95

Asn Leu Asp Asn Asn Ser Leu Tyr Thr Gln Leu Glu Met Leu Val Gln
            100                 105                 110

Gly Ala Glu Arg Leu Gln Thr Ser Ser Leu Ile Ser Pro Pro Arg Ser
        115                 120                 125

Phe Ser Met Lys Ile Ser Ser Phe Ile Ser Thr Ser Leu Pro Leu Pro
    130                 135                 140

Thr Ser Val Ser Gly Ser Ser Val Gly Glu Met Ser Gly Arg Ser
145                 150                 155                 160

Val Ser Gln Gln Lys Ser Glu Gln Tyr Ala Asn Asn Leu Ala Gly Arg
                165                 170                 175

Thr Glu Ser Pro Gln Gly Ser Ser Leu Ala Ser Arg Ile Thr Glu Lys
            180                 185                 190

Leu Ser Ser Met Ala Arg Ser Ala Ile Glu Phe Ile Lys Arg Met Phe
        195                 200                 205

Ser Glu Gly Ser His Lys Pro Val Val Thr Pro Ala Pro Thr Pro Ala
210                 215                 220

Gln Met Pro Ser Pro Thr Ser Phe Ser Asp Ser Ile Lys Gln Leu Ala
225                 230                 235                 240

Ala Glu Thr Leu Pro Lys Tyr Ile Gln Gln Leu Ser Ser Leu Asp Ala
                245                 250                 255

Glu Thr Leu Gln Lys Asn His Asp Gln Phe Ala Thr Met Lys Ile Ser
            260                 265                 270

Ser Phe Ile Ser Thr Ser Leu Pro Leu Pro Thr Ser Val Ser Gly Ser
        275                 280                 285

Ser Ser Val Gly Glu Met Ser Gly Arg Ser Val Ser Gln Gln Lys Ser
    290                 295                 300

Glu Gln Tyr Ala Asn Asn Leu Ala Gly Arg Thr Glu Ser Pro Gln Gly
305                 310                 315                 320

Ser Ser Leu Ala Ser Arg Ile Thr Glu Lys Leu Ser Ser Met Ala Arg
                325                 330                 335

Ser Ala Ile Glu Phe Ile Lys Arg Met Phe Ser Glu Gly Ser His Lys
            340                 345                 350

Pro Val Val Thr Pro Ala Pro Thr Pro Ala Gln Met Pro Ser Pro Thr
        355                 360                 365

Ser Phe Ser Asp Ser Ile Lys Gln Leu Ala Ala Glu Thr Leu Pro Lys
    370                 375                 380

Tyr Ile Gln Gln Leu Ser Ser Leu Asp Ala Glu Thr Leu Gln Lys Asn
385                 390                 395                 400

His Asp Gln Phe Ala Thr Gly Ser Gly Ile Leu Leu Arg Ala Arg Ala
```

```
                405                 410                 415
Gln Phe Pro Arg Val Cys Met Thr Leu Asp Gly Val Leu Asn Lys Glu
            420                 425                 430

Cys Cys Pro Leu Gly Pro Glu Ala Thr Asn Ile Cys Gly Phe Leu
        435                 440                 445

Glu Gly Arg Gly Gln Cys Ala Glu Val Gln Thr Asp Thr Arg Pro Trp
        450                 455                 460

Ser Gly Pro Tyr Ile Leu Arg Asn Gln Asp Asp Arg Glu Gln Trp Pro
465                 470                 475                 480

Arg Lys Phe Phe Asn Arg Thr Cys Lys Cys Thr Gly Asn Phe Ala Gly
            485                 490                 495

Tyr Asn Cys Gly Gly Cys Lys Phe Gly Trp Thr Gly Pro Asp Cys Asn
            500                 505                 510

Arg Lys Lys Pro Ala Ile Leu Arg Arg Asn Ile His Ser Leu Thr Ala
            515                 520                 525

Gln Glu Arg Glu Gln Phe Leu Gly Ala Leu Asp Leu Ala Lys Lys Ser
        530                 535                 540

Ile His Pro Asp Tyr Val Ile Thr Thr Gln His Trp Leu Gly Leu Leu
545                 550                 555                 560

Gly Pro Asn Gly Thr Gln Pro Gln Ile Ala Asn Phe Ser Val Tyr Asp
            565                 570                 575

Phe Phe Val Trp Leu His Tyr Tyr Ser Val Arg Asp Thr Leu Leu Gly
            580                 585                 590

Pro Gly Arg Pro Tyr Lys Ala Ile Asp Phe Ser His Gln Gly Pro Ala
            595                 600                 605

Phe Val Thr Trp His
            610

<210> SEQ ID NO 11
<211> LENGTH: 572
<212> TYPE: PRT
<213> ORGANISM: Artificial Sequence
<220> FEATURE:
<223> OTHER INFORMATION: Synthetic SycE-YopE-gp100

<400> SEQUENCE: 11

Met Tyr Ser Phe Glu Gln Ala Ile Thr Gln Leu Phe Gln Gln Leu Ser
1               5                   10                  15

Leu Ser Ile Pro Asp Thr Ile Glu Pro Val Ile Gly Val Lys Val

-continued

```
            145                 150                 155                 160
        Ser Gln Gln Lys Ser Asp Gln Tyr Ala Asn Asn Leu Ala Gly Arg Thr
                        165                 170                 175
        Glu Ser Pro Gln Gly Ser Ser Leu Ala Ser Arg Ile Ile Glu Arg Leu
                        180                 185                 190
        Ser Ser Met Ala His Ser Val Ile Gly Phe Ile Gln Arg Met Phe Ser
                        195                 200                 205
        Glu Gly Ser His Lys Pro Val Val Thr Pro Ala Leu Thr Pro Ala Gln
                        210                 215                 220
        Met Pro Ser Pro Thr Ser Phe Ser Asp Ser Ile Lys Gln Leu Ala Ala
        225                 230                 235                 240
        Glu Thr Leu Pro Lys Tyr Met Gln Gln Leu Ser Ser Leu Asp Ala Glu
                        245                 250                 255
        Thr Leu Gln Lys Asn His Asp Gln Phe Ala Thr Gly Ser Gly Lys Asn
                        260                 265                 270
        Thr Met Asp Leu Val Leu Lys Arg Cys Leu Leu His Leu Ala Val Ile
                        275                 280                 285
        Gly Ala Leu Leu Ala Val Gly Ala Thr Lys Val Pro Arg Asn Gln Asp
        290                 295                 300
        Trp Leu Gly Val Ser Arg Gln Leu Arg Thr Lys Ala Trp Asn Arg Gln
        305                 310                 315                 320
        Leu Tyr Pro Glu Trp Thr Glu Ala Gln Arg Leu Asp Cys Trp Arg Gly
                        325                 330                 335
        Gly Gln Val Ser Leu Lys Val Ser Asn Asp Gly Pro Thr Leu Ile Gly
                        340                 345                 350
        Ala Asn Ala Ser Phe Ser Ile Ala Leu Asn Phe Pro Gly Ser Gln Lys
                        355                 360                 365
        Val Leu Pro Asp Gly Gln Val Ile Trp Val Asn Asn Thr Ile Ile Asn
                        370                 375                 380
        Gly Ser Gln Val Trp Gly Gly Gln Pro Val Tyr Pro Gln Glu Thr Asp
        385                 390                 395                 400
        Asp Ala Cys Ile Phe Pro Asp Gly Gly Pro Cys Pro Ser Gly Ser Trp
                        405                 410                 415
        Ser Gln Lys Arg Ser Phe Val Tyr Val Trp Lys Thr Trp Gly Gln Tyr
                        420                 425                 430
        Trp Gln Val Leu Gly Gly Pro Val Ser Gly Leu Ser Ile Gly Thr Gly
                        435                 440                 445
        Arg Ala Met Leu Gly Thr His Thr Met Glu Val Thr Val Tyr His Arg
        450                 455                 460
        Arg Gly Ser Arg Ser Tyr Val Pro Leu Ala His Ser Ser Ser Ala Phe
        465                 470                 475                 480
        Thr Ile Thr Asp Gln Val Pro Phe Ser Val Ser Val Ser Gln Leu Arg
                        485                 490                 495
        Ala Leu Asp Gly Gly Asn Lys His Phe Leu Arg Asn Gln Pro Leu Thr
                        500                 505                 510
        Phe Ala Leu Gln Leu His Asp Pro Ser Gly Tyr Leu Ala Glu Ala Asp
                        515                 520                 525
        Leu Ser Tyr Thr Trp Asp Phe Gly Asp Ser Ser Gly Thr Leu Ile Ser
                        530                 535                 540
        Arg Ala Leu Val Val Thr His Thr Tyr Leu Glu Pro Gly Pro Val Thr
        545                 550                 555                 560
        Ala Gln Val Val Leu Gln Ala Ala Ile Pro Leu Thr
                        565                 570
```

<210> SEQ ID NO 12
<211> LENGTH: 491
<212> TYPE: PRT
<213> ORGANISM: Artificial Sequence
<220> FEATURE:
<223> OTHER INFORMATION: Synthetic SycE-YopE-LCMV-NP

<400> SEQUENCE: 12

```
Met Tyr Ser Phe Glu Gln Ala Ile Thr Gln Leu Phe Gln Leu Ser
1               5                   10                  15

Leu Ser Ile Pro Asp Thr Ile Glu Pro Val Ile Gly Val Lys Val Gly
                20                  25                  30

Glu Phe Ala Cys His Ile Thr Glu His Pro Val Gly Gln Ile Leu Met
                35                  40                  45

Phe Thr Leu Pro Ser Leu Asp Asn Asn Glu Lys Glu Thr Leu Leu
        50                  55                  60

Ser His Asn Ile Phe Ser Gln Asp Ile Leu Lys Pro Ile Leu Ser Trp
65                  70                  75                  80

Asp Glu Val Gly Gly His Pro Val Leu Trp Asn Arg Gln Pro Leu Asn
                85                  90                  95

Asn Leu Asp Asn Asn Ser Leu Tyr Thr Gln Leu Glu Met Leu Val Gln
                100                 105                 110

Gly Ala Glu Arg Leu Gln Thr Ser Ser Leu Ile Ser Pro Pro Arg Ser
                115                 120                 125

Phe Ser Met Lys Ile Ser Ser Phe Ile Ser Thr Ser Leu Pro Leu Pro
                130                 135                 140

Thr Ser Val Ser Gly Ser Ser Val Gly Glu Met Ser Gly Arg Ser
145                 150                 155                 160

Val Ser Gln Gln Lys Ser Glu Gln Tyr Ala Asn Asn Leu Ala Gly Arg
                165                 170                 175

Thr Glu Ser Pro Gln Gly Ser Ser Leu Ala Ser Arg Ile Thr Glu Lys
                180                 185                 190

Leu Ser Ser Met Ala His Ser Ala Ile Glu Phe Ile Lys Arg Met Phe
                195                 200                 205

Ser Glu Gly Ser His Lys Pro Val Val Thr Pro Ala Pro Thr Pro Ala
                210                 215                 220

Gln Met Pro Ser Pro Thr Ser Phe Ser Asp Ser Ile Lys Gln Leu Ala
225                 230                 235                 240

Ala Glu Thr Leu Pro Lys Tyr Met Gln Gln Leu Ser Ser Leu Asp Ala
                245                 250                 255

Glu Thr Leu Gln Lys Asn His Asp Gln Phe Ala Thr Gly Ser Phe Val
                260                 265                 270

Ser Asp Gln Val Gly Asp Arg Asn Pro Tyr Glu Asn Ile Leu Tyr Lys
                275                 280                 285

Val Cys Leu Ser Gly Glu Gly Trp Pro Tyr Ile Ala Cys Arg Thr Ser
                290                 295                 300

Ile Val Gly Arg Ala Trp Glu Asn Thr Thr Ile Asp Leu Thr Ser Glu
305                 310                 315                 320

Lys Pro Ala Val Asn Ser Pro Arg Pro Ala Pro Gly Ala Ala Gly Pro
                325                 330                 335

Pro Gln Val Gly Leu Ser Tyr Ser Gln Thr Met Leu Leu Lys Asp Leu
                340                 345                 350

Met Gly Gly Ile Asp Pro Asn Ala Pro Thr Trp Ile Asp Ile Glu Gly
                355                 360                 365
```

```
Arg Phe Asn Asp Pro Val Glu Ile Ala Ile Phe Gln Pro Gln Asn Gly
        370                 375                 380

Gln Phe Ile His Phe Tyr Arg Glu Pro Val Asp Lys Gln Phe Lys
385                 390                 395                 400

Gln Asp Ser Lys Tyr Ser His Gly Met Asp Leu Ala Asp Leu Phe Asn
                405                 410                 415

Ala Gln Pro Gly Leu Thr Ser Ser Val Ile Gly Ala Leu Pro Gln Gly
                420                 425                 430

Met Val Leu Ser Cys Gln Gly Ser Asp Asp Ile Arg Lys Leu Leu Asp
            435                 440                 445

Ser Gln Asn Arg Lys Asp Ile Lys Leu Ile Asp Val Glu Met Thr Arg
        450                 455                 460

Glu Ala Ser Arg Glu Tyr Glu Asp Lys Val Trp Asp Lys Tyr Gly Trp
465                 470                 475                 480

Leu Cys Lys Met His Thr Gly Ile Val Arg Asp
                485                 490

<210> SEQ ID NO 13
<211> LENGTH: 24
<212> TYPE: DNA
<213> ORGANISM: Artificial Sequence
<220> FEATURE:
<223> OTHER INFORMATION: Synthetic Forward Primer

<400> SEQUENCE: 13
cgggatccaa ctttcaaaca gctg                                              24

<210> SEQ ID NO 14
<211> LENGTH: 25
<212> TYPE: DNA
<213> ORGANISM: Artificial Sequence
<220> FEATURE:
<223> OTHER INFORMATION: Synthetic Reverse primer

<400> SEQUENCE: 14
ggggtacctt aagggaaac acatc                                              25

<210> SEQ ID NO 15
<211> LENGTH: 24
<212> TYPE: DNA
<213> ORGANISM: Artificial Sequence
<220> FEATURE:
<223> OTHER INFORMATION: Synthetic Forward primer

<400> SEQUENCE: 15
taggatccgg aattctgctc agag                                              24

<210> SEQ ID NO 16
<211> LENGTH: 24
<212> TYPE: DNA
<213> ORGANISM: Artificial Sequence
<220> FEATURE:
<223> OTHER INFORMATION: Synthetic Reverse primer

<400> SEQUENCE: 16
agatggtacc tttagtgcca cgtg                                              24

<210> SEQ ID NO 17
<211> LENGTH: 24
<212> TYPE: DNA
<213> ORGANISM: Artificial Sequence
<220> FEATURE:
```

<223> OTHER INFORMATION: Synthetic Forward primer

<400> SEQUENCE: 17
gaagatctgg gaagaacaca atgg                                            24

<210> SEQ ID NO 18
<211> LENGTH: 25
<212> TYPE: DNA
<213> ORGANISM: Artificial Sequence
<220> FEATURE:
<223> OTHER INFORMATION: Synthetic Reverse primer

<400> SEQUENCE: 18
ggggtacctt aggtgagagg aatgg                                           25

<210> SEQ ID NO 19
<211> LENGTH: 27
<212> TYPE: DNA
<213> ORGANISM: Artificial Sequence
<220> FEATURE:
<223> OTHER INFORMATION: Synthetic Primer

<400> SEQUENCE: 19
taccatggca tttgtttcag accaagt                                         27

<210> SEQ ID NO 20
<211> LENGTH: 28
<212> TYPE: DNA
<213> ORGANISM: Artificial Sequence
<220> FEATURE:
<223> OTHER INFORMATION: Synthetic Primer

<400> SEQUENCE: 20
taaagcttct agtcccttac tattccag                                        28

<210> SEQ ID NO 21
<211> LENGTH: 27
<212> TYPE: DNA
<213> ORGANISM: Artificial Sequence
<220> FEATURE:
<223> OTHER INFORMATION: Synthetic Primer

<400> SEQUENCE: 21
taccatggca tttgtttcag accaagt                                         27

<210> SEQ ID NO 22
<211> LENGTH: 28
<212> TYPE: DNA
<213> ORGANISM: Artificial Sequence
<220> FEATURE:
<223> OTHER INFORMATION: Synthetic Primer

<400> SEQUENCE: 22
taaagcttct agtcccttac tattccag                                        28

<210> SEQ ID NO 23
<211> LENGTH: 22
<212> TYPE: DNA
<213> ORGANISM: Artificial Sequence
<220> FEATURE:
<223> OTHER INFORMATION: Synthetic Forward primer

<400> SEQUENCE: 23
gtgtcaaagt tgggaattc gc                                               22

```
<210> SEQ ID NO 24
<211> LENGTH: 22
<212> TYPE: DNA
<213> ORGANISM: Artificial Sequence
<220> FEATURE:
<223> OTHER INFORMATION: Synthetic Reverse primer

<400> SEQUENCE: 24
ctgctggatc ctgacactga tg                                              22

<210> SEQ ID NO 25
<211> LENGTH: 9
<212> TYPE: PRT
<213> ORGANISM: Artificial Sequence
<220> FEATURE:
<223> OTHER INFORMATION: Synthetic LCMV-NP

<400> SEQUENCE: 25

Phe Gln Pro Gln Asn Gly Gln Phe Ile
1               5
```